US008765364B2

(12) United States Patent
Curtis et al.

(10) Patent No.: US 8,765,364 B2
(45) Date of Patent: *Jul. 1, 2014

(54) EX VIVO METHODS FOR VALIDATING SUBSTANCE TESTING WITH HUMAN ORGANS AND/OR TISSUES

(75) Inventors: Gerald Curtis, Cardiff (GB); John Brassil, Northbrook, IL (US); David Kravitz, South Barrington, IL (US)

(73) Assignee: Lifeline Scientific, Inc., Des Plaines, IL (US)

( * ) Notice: Subject to any disclaimer, the term of this patent is extended or adjusted under 35 U.S.C. 154(b) by 584 days.

This patent is subject to a terminal disclaimer.

(21) Appl. No.: 11/802,064

(22) Filed: May 18, 2007

(65) Prior Publication Data

US 2008/0286747 A1 Nov. 20, 2008

(51) Int. Cl.
*A01N 1/00* (2006.01)

(52) U.S. Cl.
USPC .............................................. 435/1.2; 435/1.1

(58) Field of Classification Search
None
See application file for complete search history.

(56) References Cited

U.S. PATENT DOCUMENTS

| | | |
|---|---|---|
| 3,877,843 A | 4/1975 | Fischel |
| 4,618,586 A | 10/1986 | Walker |
| 4,629,686 A | 12/1986 | Gruenberg |
| 4,666,425 A | 5/1987 | Fleming |
| 5,051,352 A | 9/1991 | Martindale et al. |
| 5,217,860 A | 6/1993 | Fahy et al. |
| 5,328,821 A | 7/1994 | Fisher et al. |
| 5,338,662 A | 8/1994 | Sadri |
| 5,494,822 A | 2/1996 | Sadri |
| 5,622,429 A | 4/1997 | Heinze |
| 5,989,918 A | 11/1999 | Dietz et al. |
| 6,023,630 A | 2/2000 | Bacchi et al. |
| 6,024,698 A | 2/2000 | Brasile |
| 6,046,046 A | 4/2000 | Hassanein |
| 6,197,575 B1 | 3/2001 | Griffith et al. |
| 6,582,953 B2 | 6/2003 | Brasile |
| 6,592,567 B1 | 7/2003 | Levin et al. |
| 6,673,594 B1 | 1/2004 | Owen et al. |
| 6,699,231 B1 | 3/2004 | Sterman et al. |
| 6,953,655 B1 | 10/2005 | Hassanein et al. |
| 7,410,474 B1 | 8/2008 | Friend et al. |
| 2002/0123141 A1 | 9/2002 | Hariri |
| 2004/0002891 A1 | 1/2004 | Chen et al. |
| 2004/0038193 A1 | 2/2004 | Brasile |
| 2004/0224298 A1 | 11/2004 | Brassil et al. |
| 2005/0015278 A1 | 1/2005 | Ghouri |
| 2005/0255458 A1 | 11/2005 | Polansky |
| 2005/0276792 A1 | 12/2005 | Kaminski et al. |
| 2006/0019326 A1 | 1/2006 | Vacanti et al. |
| 2007/0072222 A1 | 3/2007 | Boess et al. |

FOREIGN PATENT DOCUMENTS

| | | |
|---|---|---|
| EP | 1 208 748 A1 | 8/2000 |
| JP | 2-258701 | 10/1990 |
| WO | WO 88/05261 A1 | 7/1988 |
| WO | WO 94/06292 | 3/1994 |
| WO | WO 95/31897 | 11/1995 |
| WO | WO 96/31779 | 10/1996 |
| WO | WO 98/09166 | 3/1998 |
| WO | WO 99/35245 | 7/1999 |
| WO | WO 99/45982 | 9/1999 |
| WO | WO 00/18226 | 4/2000 |
| WO | WO 02/26034 A2 | 4/2002 |
| WO | WO 2005/074681 A2 | 8/2005 |

OTHER PUBLICATIONS

Roediger W.E.W. et al. Effect of short-chain fatty acid on sodium absorption in isolated human colon perfused through the vascular bed. Digestive Diseases and sciences, Feb. 1981, vol. 26, No. 2, pp. 100-106.*
Desai T.R. et al. Defining the critical limit of oxygen extraction in the human small intestine, Journal of Vascular Surgery, 1996, vol. 23, No. 5, pp. 832-838.*
Coleman R.A. et al. Use of human tissue in ADME and safety profiling of development candidates, DDT, Nov. 2001, vol. 6, No. 21, pp. 1116-1126.*
Svensson, U. S. H. et al. High in situ rat intestinal permeability of artemisinin unaffected by multiple dosing and with no evidence of p-glycoprotein involvement, Drug Metabolism and Disposition, 1999, vol. 27, No. 2, pp. 227-232.*
Nov. 24, 2009 International Preliminary Report on Patentability issued in International Patent Application No. PCT/US2008/006369.
Takahashi H. et al., "The Use of a Perfluorochemical Emulsion as a Vascular Perfusate in Drug Absorption", Journal of Pharmacy and Pharmacology, Pharmaceutical Press, vol. 40, No. 3, Apr. 1, 1988, pp. 252-257.
U.S. Appl. No. 11/598,800, filed Nov. 14, 2006, Brassil et al.
U.S. Appl. No. 11/802,059, filed May 18, 2007, Curtis et al.
"Human Data Before Human-Trials Improving Drug Discovery and Development Productivity with Ex Vivo Metrics," Katzenbach Partners LLC, 2005, pp. 1-22.
"Perfusion of the isolated rat liver," Curtis, C.G. et al., Proceedings of the Physiological Society, Dec. 1970, pp. 14P-15P.
"Degradation of [³H]Chondroitin 4-Sulphate and Re-utilization of the [³H]Hexosamine Component by the Isolated Perfused Rat Liver," Macnicholl, Alan D. et al., Biochem. J. (1980), vol. 186, pp. 279-286.
"Utilization by the Isolated Perfused Rat Liver of N-Acetyl-D-[1-¹⁴C]galactosamine and N-[³H]Acetyl D-galactosamine for the Biosynthesis of Glycoproteins," MacNicoll, Alan D. et al., Biochem. J.. (1978) vol. 174, pp. 421-426.
"NMR study of the whole rat bile: the biliary excretion of 4-cyano-N, N-dimethyl aniline by an isolated perfused rat live and a liver in situ," Ryan, David A. et al., *Journal of Pharmaceutical & Biomedical Analysis*, 1995, vol. 13, No. 6, pp. 735-745.
"Liver as major organ of phenol detoxication?," Powell, G. et al., *Nature*, Nov. 15, 1974, vol. 252, pp. 234-235.

(Continued)

Primary Examiner — Satyendra Singh
(74) Attorney, Agent, or Firm — Oliff PLC

(57) ABSTRACT

Methods of validating results of assessments of test substances using human-derived tissues and/or organs, particularly tissues and/or organs unsuitable for transplantation, include assessing the suitability of the organ and/or tissue for substance testing, as well as inter-organ variability and use of exogenous and/or endogenous controls.

42 Claims, No Drawings

(56) References Cited

OTHER PUBLICATIONS

"Oxidation of Sodium Sulphide by Rat Liver, Lungs and Kidney," Bartholomew, Terrence C. et al., *Biochemical Pharmacology*, 1980, vol. 29, pp. 2431-2437.
"The metabolic sulphation of polyethyleneglycols by isolated perfused rat and guinea-pig livers", Roy, A. B. and Maggs, J. et al., *Xenobiotica*, 1987, vol. 17, No. 6, pp. 725-732.
"Octan-2-sulphate degradation in the isolated perfused rat liver", Maggs, J. et al., *Biochemical Pharmacology*, 1984, vol. 33, No. 5, pp. 827-829.
*Isolated Perfused Liver Technology for Studying Metabolic and Toxicological Problems*, Powell, G.M. et al., 1989, vol. 7, No. 1, pp. 53-86.
"Organ Perfusion and Mass Spectrometry: A Timely Merger for Drug Development," Curtis, C. Gerald et al., *Current Topics in Medicinal Chemistry*, 2002, vol. 2, pp. 77-86.
*The Use of Isolated Perfused Organs*, Curtis, C. G. et al., pp. 295-302, Metabolism of Xenobiotics,1988.
"Predictive Models for Tissue Metabolism-Screening Using Organ Perfusion Methods," Curtis, G., CPSA Digest 2001, http://www.milestonedevelopment.com/CPSA/2001/day3oa3.html, downloaded Feb. 10, 2007.
"Alterations of the renal function in the isolated perfused rat kidney system after in vivo and in vitro application of S-(1,2-dichlorovinyl)-L-cysteine and S-(2,2-dichlorovinyl)-L-cysteine," Ilinskaja, O. and Vamvakas, S., Arch Toxicol (1996), vol. 70, pp. 224-229.
A New Paradigm in Perfusion, http://res-del.com/resources/AQIX_RS-I, Anonymous, 2003; http://www.aqix.com/about_RDI.htm. downloaded Aug. 11, 2006.
"The Rate of Induction of Hypothermic Arrest Determines the Outcome in a Swine Model of Lethal Hemorrhage," Alam, H. et al., *The Journal of Trauma Injury, Infection, and Critical Care*, Nov. 2004, vol. 57, No. 5, pp. 961-969.
"Machine Perfusion of Isolated Kidney At 37° C. Using Pyridoxalated Hemoglobin-Polyoxyethlene (PHP) Solution, UW Solution and its Combination", T. Horiuchi et al., *Biomaterials, Art. Cells & Immob. Biotech*, vol. 20, Nos. 2-4,, pp. 549-555, 1992.
"In Situ Cadaver Kidney Perfusion", Robert T. Schweizer et al., *Transplantation*, vol. 32, No. 6, pp. 482-484, Dec. 1981.
"Intermediate Normothermic Perfusion During Cold Storage of Ischemically Injured Kidneys", J.G. Maessen et al., *Transplantation Proceedings*, vol. 21, No. 1, pp. 1252-1253, Feb. 1989.
"Perfusion of Rabbit Kidneys With Glycerol Solutions At 5° C.", D.E. Pegg et al., *Cryobiology*, vol. 14, pp. 168-178, 1977.
"Seleno-DL-Methionine Reduces Freezing Injury in Hearts Protected With Ethanediol", W.J. Armitage et al., *Cryobiology*, vol. 18, pp. 370-377, 1981.
"Banking of Cells, Tissues, and Organs at Low Temperatures", David E. Pegg, *Current Trends in Cryobiology*, Plenum Press, NY, pp. 153-180, 1970.
"Effect of Pharmacologic Agents on the Function of the Hypothermicall Preserved Dog Kidney During Normothermic Reperfusion", Rutger J. Ploeg et al., *Surgery*, vol. 103, No. 6, pp. 676-682, Jun. 1988.
"Is Normothermic Preservation an Alternative to Hypothermic Preservation?", R. N. Dunn et al., *Organ Preservation Basic and Applied Aspects*, Chapter 38, pp. 273-277, 1982.
"Free Radicals and Myocardial Ischemia and Reperfusion Injury", Paul J. Simpson et al., *J Lab Cin Med.*, pp. 13-30, Jul. 1987.
M.R. Buhl et al. "The Postanoxic Regeneration of 5'-Adenine Nucleotides in Rabbit Kidney Tissue during In Vitro Perfusion," 1976, pp. 175-181.

"Organko Servierungsmachine OKM 82", Von Dietmer Scholz et al., East German Article, 1983, Medizintechnik, 1983, vol. 23, issue 1, pp. 2-5.
"MOX®-100 Renal Preservation System", Waters Instruments Medical Group, pp. 2-7, 1982.
"Organ Perfusion Systems: An Evaluation Criteria", Fereydoon Sadri, Ph.D., *T.O.P.S. Medical Corporation*, pp. 1-8, 1987.
Apr. 26, 2011 Final Office Action issued in U.S. Appl. No. 11/802,059.
Feb. 10, 2011 European Search Report issued in GB0921330.7.
Mar. 25, 2011 European Search Report issued in GB0921349.7.
Jun. 28, 2011 Office Action issued in U.S. Appl. No. 11/598,800.
Dec. 21, 2011 Final Rejection issued in U.S. Appl. No. 11/598,800.
Mar. 17, 2010 Office Action issued in U.S. Appl. No. 10/845,154.
Feb. 3, 2011 Restriction Requirement issued in U.S. Appl. No. 11/598,800.
Nov. 12, 2010 Office Action issued in U.S. Appl. No. 11/802,059.
Jul. 29, 2010 Election of Species Requirement issued in U.S. Appl. No. 11/802,059.
May 16, 2011 Office Action issued in U.S. Appl. No. 10/845,154.
Apr. 1, 2009 Office Action issued in U.S. Appl. No. 10/845,154.
Nov. 1, 2007 Office Action issued in U.S. Appl. No. 10/845,154.
Feb. 8, 2007 Office Action issued in U.S. Appl. No. 10/845,154.
Aug. 6, 2008 Office Action issued in U.S. Appl. No. 10/845,154.
U.S. Appl. No. 10/845,154, filed May 14, 2004 to Brassil et al.
Sep. 6, 2011 European Office Action issued in EP 05 817 022.6.
Malgorzata Tokarska-Schlattner, et al., "Acute toxicity of doxorubicin on isolated perfused heart: response of kinases regulating energy supply," Am J Physiol Heart Circ Physiol, vol. 289, pp. H37-47, Mar. 11, 2005.
Bell Jr. R.H. et al., "Ex-vivo isolated perfusion of the pancreas in the Syrian golden hamster," international Journal of Pancreatology, 1 (1986), pp. 71-81.
Jul. 29, 2008 International Search Report issued in PCT/US2008/006368.
Feb. 28, 2006 International Search Report issued in PCT/US2005/016057.
Oct. 18, 2011 United Kingdom Office Action issued in GB0921349.7.
Oct. 18, 2011 United Kingdom Office Action issued in GB0921330.7.
Dec. 5, 2011 Office Action issued in U.S. Appl. No. 10/845,154.
Dec. 7, 2011 Office Action issued in U.S. Appl. No. 11/802,059.
TUBEROSE.COM—Environmental Toxicity, published online Feb. 4, 2005 on the web at http://tuberose.com/Environmental_Toxicity.html, pp. 1-8.
D.K. Hansen et al., "Pharmacokinetic and Metabolism Studies Using Microdialysis Sampling," J. Pharmaceutical. Sciences, Jan. 1999, vol. 88, No. 1, pp. 14-27.
G. Nowak et al., "Metabolic Changes in the Liver Graft Monitored Continuously With Microdialysis During Liver Transplantation in a Pig Model," Liver Transplantation, May 2002, vol. 8, No. 5, pp. 424-432.
S.C. Baicu et al., "Interstitial Fluid Analysis for Assessment of Organ Function," Clin. Transplant, Jun. 24, 2004, vol. 18, No. 12, pp. 16-21.
Sep. 26, 2013 Office Action issued in Chinese Patent Application No. 2013092300947840 (with translation).
Oct. 23, 2013 Office Action issued in U.S. Appl. No. 11/598,800.
May 21, 2012 Office Action issued in U.S. Appl. No. 11/802,059.
Mar. 28, 2013 Chinese Office Action issued in Chinese Patent Application No. 200880024743.5 (with translation).

\* cited by examiner

EX VIVO METHODS FOR VALIDATING SUBSTANCE TESTING WITH HUMAN ORGANS AND/OR TISSUES

BACKGROUND

This disclosure relates to methods for validating qualitative and quantitative results of assessments of properties, fates and effects of substances and organs and/or tissues contacted by them, such as absorption, transport, metabolism, elimination, efficacy and/or toxicity of substances, such as chemical compounds and, particularly, drugs and drug candidates, when perfusing human-derived organs and/or tissues ex vivo with compatible perfusate solutions containing such substances. Methods of the invention permit validating results of such assessments using human-derived organs and/or tissues, particularly human organs and tissues unsuitable for transplantation, on an organ-by-organ or tissue-by-tissue basis.

Methodologies available for assessing substances and human organs and/or tissue affected by them span many levels of mammalian organization from in vivo studies to studies of isolated organs or tissues, tissue slices, cultured cell types, subcellular particles, multi-enzyme complexes and molecular interactions. In practice, these complex methods often result in considerable wasted time, effort and resources in many fields, particularly drug development, where drug candidates may undergo several rounds of safety and efficacy testing yet later testing or market experience reveals undesirable effects, sometimes with tragic consequences. For example, drugs that have been approved for human use but later recalled due to toxicity issues include COX-2 inhibitors, phexophenadine and thalidomide.

In early clinical trials, adverse benefit/risk ratios frequently cause the demise of otherwise promising pharmacologically active substances. Such events are costly and can have a profound effect on drug discovery, health care and industry stability. Historically, attempts to weed-out substances having an unacceptable benefit/risk ratio have relied on in vivo non-human animal studies using several species, such as rodent species. However, unlike inbred strains of animals used in drug development, the target species, i.e., humans, is, by comparison, very diverse in form and function. Thus, the quantitative and qualitative properties, fates and effects of substances, such as drug candidates and drugs, are also very diverse.

Limitations of toxicity studies in non-human species have long been, and still are, well recognized in the pharmaceutical industry, but short of performing toxicity studies in humans in vivo, there has been no viable alternative. As it is not ethical to use humans for exploratory toxicity testing, the choice has been to perform in vivo testing on a variety of non-human animal species and/or in vitro testing using human biological samples. Attempts have been made to bridge the gap between non-human testing results and effects in humans using tissue preparations containing subcellular particles, e.g., microsomes, primary cells and cells in culture, e.g., hepatocytes, and tissue slices. Although these in vitro tissue preparations generate much useful data, many drug candidates still fail in clinical trials because of adverse risk issues. There is ample evidence in the literature to suggest that this is due, at least in part, to the fact that the farther the tissue preparation is from the whole organism, the greater the risk of false positives and false negatives. For example, false positives or false negatives may occur when assessing whether test substances administered in therapeutic doses are toxic when administered alone or with other co-administered drugs. It is recognized that the confidence in the safety and efficacy of a drug compound increases as it moves from preclinical to clinical testing. It is also recognized, however, that the dangers of unforeseen deleterious results also increase. There is simply no guarantee that pharmacokinetic/toxicity relationships in normal human tissues determined in vitro will be the same as in diseased human tissues in vivo.

It is often difficult, if not impossible, to obtain samples from living human donors for drug development purposes. Unfortunately, samples from deceased donors have increased potential and actual levels of variability due to diseases and/or injuries that may or may not be related to the donor's death and/or due to variable levels of degradation after donation. Thus, it has been difficult to confidently generalize from data based on such human samples, especially at a level required for drug development. Furthermore, human samples have much more variability compared to samples from in-bred test animals.

U.S. Pat. No. 5,338,662 discloses methods for determining the effect of a test substance on an ex vivo organ. However, these methods rely on comparison to a simultaneously perfused control organ. While such methods may be suitable for organs of uniform nature and quality, such as organs from in-bred test animals, they do not account for the variability inherent in the use of human samples, especially from pre-deceased donors.

Thus, there is a need for improved methods for assessing and validating the results of assessments of substances that bridge the gap between in vivo non-human animal testing and human administration. There is a need for standardized validation testing of organs and tissues used to test substances, such as drug candidates. In addition, there is a need, in the drug development industry, for new and improved methods of validating the evaluation of potential drug candidates early in the research and development process, for providing reliable evaluations to drug development companies.

SUMMARY

Embodiments of the invention fulfill needs for validating the results of assessments of properties, fates and effects of substances and organs and/or tissues contacted by them, such as absorption, transport, metabolism, elimination, efficacy and/or toxicity and other tests of substances, such as drug candidates, using perfused tissues or organs, preferably, perfused human-derived tissues or organs, more preferably, perfused human organs and organ sets. Methods of the invention provide improved access to information and substance/effect correlations.

Embodiments include methods for assessing the suitability of organs or tissues, preferably, human organs or tissues, more preferably, human organs, and, most preferably, human organs unsuitable for transplantation including diseased or otherwise defective organs or organs having a lower than acceptable likelihood of successful transplantation, which may be determined before or after donation and/or storage, due to, inter alia, prolonged warm ischemia times, disease, injury and/or prolonged storage, for substance testing.

Embodiments include methods of assessing an organ's or tissue's physiology after its procurement, cold storage and normothermic perfusion. In embodiments, the invention provides methods for assessing the suitability of an organ or tissue, comprising:

a) perfusing at least one tissue or organ with a medical fluid that does not comprise the test substance; and b) assessing the suitability of the organ or tissue for substance testing.

Preferably, the organ or tissue is a human organ or tissue.

Preferably, the organ or tissue is perfused under physiological temperature, pressure, oxygenation, osmolality, electrolyte balance and pH.

In embodiments, assessments of suitability are based on physiology, ischemic injury and/or reperfusion injury by evaluating the perfusate, excretory/secretory fluids and/or tissue samples.

To capture organ or tissue variability and/or evaluate the properties, fates and effects of test substances, in embodiments, the invention further provides ex vivo methods comprising:

c) perfusing at least one organ or tissue with a medical fluid in the presence of at least one test substance; and d) assessing target properties of or effects of the organ or tissue such as variability and/or the absorption, transport, metabolism, elimination, efficacy and/or toxicity of the test substance on the organ or tissue, wherein variability may be assessed by quantitatively monitoring endogenous components throughout the perfusion. Exogenous controls may also or alternatively be added to the perfusate before, during and/or after the test substance is added to allow for such assessment.

Methods provided by the invention advantageously avoid inherent species differences in test substance absorption, transport, metabolism, elimination, efficacy, toxicity, tissue susceptibility and other properties and/or effects encountered when using non-human animal models to mimic in vivo activity and behavior in humans. In addition, potentially highly varied perfused human organs or tissues can be exposed to substances such as drugs or drug candidates and metabolites thereof under physiological conditions and at clinically relevant concentrations to all cell types in the organ or tissue, thereby providing more reliable, accurate and consistent results.

Human organs and tissues assessed ex vivo for suitability for substance testing may act as their own controls by the addition and monitoring of exogenous controls before, during and/or after a drug candidate and/or by monitoring of endogenous components throughout the perfusion. In this way, instead of reflecting individual variability, the data generated on the properties, fates and effects of substances such as drug candidates in corresponding organs or tissues from different donors can be normalized.

Embodiments of the present invention may be used in methods for evaluating a substance comprising passing a substance to be evaluated through a metabolically active human organ or tissue, collecting data from the organ or tissue and using the collected data to evaluate the substance.

In embodiments, the evaluation is part of a governmental and/or regulatory approval process; and data are collected by evaluating a perfusate that comprises the substance and has exited the organ or tissue or by evaluating a biopsy taken from the organ or tissue.

In embodiments, the evaluation method comprises passing a second substance through the organ or tissue after the first substance and collecting data on the interaction of the first and second substances.

In embodiments, the evaluation method comprises perfusing the organ or tissue with a first fluid that does not contain the substance and then with a second fluid that contains the substance.

Embodiments of uses of the invention include use in methods of collecting data as part of a governmental regulatory approval process comprising: providing an isolated metabolically active human organ or tissue; perfusing through the organ or tissue a perfusate containing a test substance to be evaluated; collecting data from the perfusate and organ or tissue; and using data collected as part of a submission to a governmental regulatory organization.

In embodiments, methods comprise using the data as part of a process to resolve conflicting data across species, assess a compound's toxicity, determine the presence of metabolites, and/or assess a compound's bioavailability, absorption, therapeutic effects and/or substance-substance interactions.

Embodiments of the invention may be used in methods of developing pharmaceutical products comprising passing a drug candidate through a metabolically active ex vivo human organ or tissue; collecting data from the organ or tissue; and using collected data as part of an evaluation to determine whether to continue developing the drug candidate into a pharmaceutical. The data can be used to evaluate at least one parameter of the drug candidate including those selected from the group consisting of: absorption, toxicity, drug-drug interactions, therapeutic effects, presence of metabolites and liver clearance. The data may be used, for example, in at least one drug development phase selected from the group consisting of: discovery, pre-clinical, phase I, phase II, phase III and phase IV.

Embodiments of the invention may be used in methods of generating revenue comprising charging a fee to a third party for performing an evaluation process on a drug candidate; passing the drug candidate through a metabolically active ex vivo human organ or tissue; collecting data from the organ or tissue; and providing the data to the third party.

In methods of generating revenue, data can be provided in raw form or evaluated before it is provided to the third party. The data can be used as part of a governmental and/or regulatory submission. The data can be owned by the party performing the evaluation or the party requesting the evaluation. The data can be used by the third party during at least one drug development phase selected from the group consisting of: discovery, pre-clinical, phase I, phase II, phase III and phase IV. The fee may be a lump sum payment or a percentage of sales of the resulting pharmaceutical.

Embodiments of the invention may be used in methods of reducing the cost to develop pharmaceuticals comprising screening compounds by passing the compounds through at least part of a metabolically active ex vivo human organ or tissue and determining whether to pursue pharmaceutical development of the compound. Thus, methods of reducing the cost can include not developing a pharmaceutical based, at least in part, on data generated by passing the compound through the organ or tissue and/or ranking potential pharmaceuticals based on data generated by the screening process.

Embodiments may be used in methods of developing generic pharmaceuticals comprising generating data for inclusion in a submission of a generic pharmaceutical approval process by passing a pharmaceutical through a metabolically active ex vivo human organ or tissue.

Embodiments provide information products. Such information products may comprise data relating to a pharmaceutical product that is generated, at least in part, by passing the pharmaceutical product through a metabolically active ex vivo human organ or tissue. In embodiments, the information product is provided in a computer-readable form.

Embodiments provide methods of marketing an information product comprising providing to a third party an evaluation of at least one economic effect of the information product on the development of a pharmaceutical by the third party.

In embodiments of methods of marketing, evaluation of the economic effect of the information product may be based on assumptions, wherein the evaluation may include an economic effect of the information product on a problem encountered during development of a test substance and/or a product containing such a substance. The economic effect may include a total value of the information product, which may be adjusted for the probability that the total value will be achieved. The total value of the information product may include additional profits from sales of the substance or product as a pharmaceutical, for example, where the pharmaceutical would not have been launched without the information product. The total value of the information product may also include an amount of additional peak sales of the substance or product from a decrease in time to develop the substance or product due to the information product. The decreased time to develop the substance or product may include, at least in part, time to resolve a problem encountered during development. In addition, the total value of the information product may include decreased costs to develop the substance or product due to the information product. Decreased costs may be due, at least in part, to testing obviated by the information product.

Embodiments may be used in methods of evaluating a substance, comprising: providing a substance to be evaluated and analyzing data collected from passing the substance through a metabolically active ex vivo human organ or tissue.

In embodiments of methods of evaluating a substance, the substance may be a pharmaceutical. The data may be used as part of a submission to a governmental and/or regulatory organization, as part of a process to resolve conflicting data across species or to assess the presence of metabolites or the compound's bioavailability, absorption, therapeutic effects, drug-drug interactions and/or liver clearance. In addition, the data may be used to select appropriate patients for testing the substance in clinical trials and/or to select the formulation of the substance that should be used in clinical trials.

Additional features and advantages of the present invention are described in, and will be apparent from, the following detailed description of embodiments.

DETAILED DESCRIPTION OF EMBODIMENTS

Embodiments of the invention include methods for using organs or tissues, preferably, human organs or tissues, more preferably, human organs, to: (1) assess the suitability of an organ or tissue for substance testing; (2) assess organ or tissue variability in ex vivo substance testing; (3) determine properties, fates and effects, such as the absorption, transport, metabolism, elimination, efficacy and/or toxicity, of a compound or substance, preferably a chemical compound, more preferably, a pharmaceutical drug or drug candidate; and/or (4) validate the results of substance testing based on (1) and/or (3).

Preferred organs and tissues include, but are not limited to, liver, lung, kidney, intestine, heart, pancreas, spleen, testes, placenta, thymus, thyroid, adrenal gland, arteries, veins, lymph nodes, bone, skeletal muscle, exocrine/endocrine glands, or male or female reproductive tissue and organs. Alternatively, controlled combinations of organs and/or tissues, whereby the perfusate effluent from one organ and/or tissue forms the perfusate influx for a different organ and/or tissue, or whereby organs and/or tissues are perfused by a common perfusate in parallel, may be used. The preferred organ or tissue is a metabolically active human organ or tissue that has been permanently removed from its origin, an engineered organ or tissue derived from isolated and/or cultured human cells (collectively referred to herein as human organ(s) or tissue(s) except where otherwise specified). The isolated and/or cultured human cells may comprise stem cells.

As used herein, the terms "absorption," "transport," "metabolism" and "elimination" are understood to apply to any organ or tissue employed, but are particularly relevant to certain organs and tissues used in perfusion-based testing. For example, absorption is particularly relevant to the intestines and lungs; whereas transport, such as plasma clearance and metabolism, although also relevant to the intestines and lungs, is particularly relevant to the liver, kidneys and heart. Elimination is particularly relevant to the intestines, liver, kidneys and lungs.

As used herein, the term "toxicity" encompasses physical, chemical, biochemical and biological damage to organs or tissues, including at the cellular level. Toxicity is related to deleterious effects on organs and tissues, including, but not limited to cell death, apoptosis, genetic mutation, changes in gene expression, biochemical inhibition, reductions in metabolism, induction, repression and oxidative damage, as well as deleterious effects resulting from drug-drug interactions. As provided herein, embodiments of the invention include methods that involve detecting organ- or tissue-specific biomarkers for acute or chronic toxicity induced by a test compound, such as a drug or drug candidate.

The term "efficacy" encompasses a measure of the positive, homeostatic or health-promoting effects of a test compound, such as a drug or drug candidate, on a tissue or organ, preferably, human tissue or organ. Such measures include, but are not limited to, assays for reducing or eliminating disease-specific biomarkers, preferably using diseased organs or organs infected by a pathogen. In certain embodiments, the biomarker is a pathogen-associated marker of either pathogen or cellular origin, the reduction or elimination of which indicates that the test compound may be effective as an anti-pathogenic agent. Conversely, in embodiments, the biomarker may be a breakdown product or other indicator of an anti-pathogenic effect, wherein an increase in the biomarker evidences the efficacy of the test compound as an anti-pathogenic agent. Thus, evaluating different tissues or organs with a test compound may provide evidence of the compound's efficacy and/or beneficial effects.

The terms "substance," "test substance," "test compound," and "compound" are used interchangeably and except as otherwise specified include, but are not limited to, drug- or pharmaceutical-related substances such as drug candidates and pharmaceuticals and also non-drug- or pharmaceutical-related substances such as environmental substances, such as smoke and other industrial effluents; agricultural products and by-products; building materials; manufacturing products and by-products; food products such as food processing products and by-products, foods and food additives; tobacco products such as cigarette, cigar or pipe smoke or chewing tobacco extracts and components thereof; cleaning products such as detergents, bleaches, soaps, shampoos and conditioners; cosmetics such as skin, hair and nail cosmetics; etc., as described in simultaneously filed co-pending U.S. patent application Ser. No. 11/802,059, the entire contents of which are incorporated herein by reference in their entirety.

As used herein, "normothermic conditions" refers to temperatures in the range of 37±3° C.

Perfusion preservation is applied routinely to organs for clinical transplant, wherein perfusion at hypothermic arrest (about 4° C. to about 8° C.) is the preferred method of preservation. In contrast, organ preservation for transplant under physiologic conditions, including normal body temperature (normothermia), although studied at length, has not been clinically applied because it is difficult in practical applications to maintain an organ at normal body temperature. To some extent, the application of normothermia has been limited by the high demands placed on a transplanted organ, specifically that it be both maximally functional and minimally inflammatory. Because demands of transplantation are reduced or non-existent in ex vivo methods of the invention, many of the limitations of normothermia are overcome. Specifically, ex vivo normothermic organs or tissues may be supplied with oxygen via type-matched blood cells without concerns of immunogenicity, and may acceptably experience degraded functionality during normothermic perfusion, e.g., as toxins normally cleared by other organs or tissues accumulate and as substrates and factors normally produced by other organs or tissues are depleted. However, the organs and tissues should be and remain suitable for the purpose for which the methods are performed.

Suitability determination embodiments include methods of assessing an organ's or tissue's physiology after its procurement, cold storage and normothermic perfusion. In embodiments, the invention provides methods for testing with a test substance, comprising:

a) perfusing at least one organ or tissue with a medical fluid that does not comprise the test substance; and b) assessing the suitability of the organ or tissue for substance testing.

In embodiments, the organ or tissue is perfused under physiological temperature, pressure, oxygenation, osmolality, electrolyte balance and pH. Preferably, the perfusate comprises matched human erythrocytes in a physiologically-acceptable medical fluid. The medical fluid advantageously further comprises about 2 to about 6% human serum albumin, N-acetylcysteine, adenosine monophosphate (AMP) and superoxide dismutase. In certain organs, such as the heart, intestine and liver, nervous stimulation may be provided as well during perfusion. In embodiments, such as wherein the organ is a liver, the medical fluid may comprise endogenous hormones and bile acids. In embodiments, such as wherein the organ is a kidney, the medical fluid may comprise a mixture of essential and non-essential amino acids. In embodiments, such as wherein the organ is intestine, the medical fluid may comprise dexamethasone or noradrenaline.

In embodiments, assessments of suitability are based on physiological functions, ischemic injury and/or reperfusion injury by evaluating the perfusate, excretory fluids and/or tissue samples. Preferably, the perfusion effluent is a functional effluent depending on the organ, such as kidney urine, liver bile or lung mucus or an effluent comprising pancreatic exocrine digestive enzymes. In embodiments, the effluent may be assayed after it is recovered from a source leaving the organ via a vein, such as insulin or glucagons from the pancreas, albumin or glucose from the liver, oxygen or carbon dioxide from the lung, or creatinine from the kidney. In the heart and intestine, validation may involve assessing a motor response, such as heartbeat and peristalsis, respectively. Additionally, validation in any organ may involve vascular resistance, and, in the lungs, changes in respiratory functions including compliance, resistance, tidal volume, and peak airway pressure.

To capture organ variability and/or evaluate the properties, fates and effects of test substances, in embodiments, the invention further provides ex vivo methods comprising:

c) perfusing at least one organ or tissue with a medical fluid in the presence of at least one test substance; and d) assessing organ or tissue variability and/or effects and fates of the substance such as the absorption, transport, metabolism, elimination, efficacy or toxicity of the test substance on the organ or tissue. Variability may be assessed by quantitatively monitoring endogenous components throughout the perfusion. Exogenous controls may alternatively or in addition be added to the perfusate before, during and/or after the test substance is added to allow for such assessment.

As described above, embodiments of methods include a preservation stage in which one or more organs or tissues derived from a target species, such as a human, are preserved under hypothermic conditions such that the organs or tissues are intended to maintain the capacity to resume and sustain substantially normal metabolic activity and function upon return to physiologic temperature. As used herein, the term "metabolically active" refers to demonstrating a level of biochemical activity characteristic of a living organism.

In a functional stage, organs or tissues may be perfused with a normothermic blood, blood-based or synthetic perfusate to stabilize the organ or tissue physiology. The physiology and biochemistry of the organ or tissue is preferably maintained substantially in accordance with the physiology and biochemistry of an organ or tissue in vivo, such that data generated from the testing is substantially unequivocal, reproducible and relevant. In whole organs, for example, cells retain their phenotypes, cell types are present in their normal proportions and orientations with respect to blood and tissue, and compounds are delivered as they would be delivered in vivo.

The functional state of test organs or tissues may be quantified with positive and/or negative controls. The controls may be added before, simultaneously with or after the test substance or after substantially all the essential samples required for analysis of the properties, fate and effects of test substances have been collected. A fluid or perfusate that does not contain the test substance may be passed through the organ or tissue before and/or after perfusing the organ or tissue with a fluid that contains the test substance. In this way, the organ or tissue may act as its own control. The positive and/or negative endogenous and/or exogenous controls used depend on the primary objective of each study.

Embodiments of methods may be conducted in "normal," "diseased" or injured organs or tissues (including organs or tissues subject to perfusion injury and organs or tissues subject to pre-donation disease and/or injury), wherein the physiology and biochemistry of each organ or tissue is maintained as close as possible to in vivo characteristics and properties for the particular disease or condition. Embodiments of methods may comprise use of multiple medical devices, solutions and protocols, including sourcing, procuring, preserving and evaluating research organs and/or tissues.

Maintaining in vivo characteristics of ex vivo organs and tissues involves evaluating organ or tissue characteristics considered to be "normal," such that information relating to the fates and effects of substances, such as drug candidates, is based on the organ or tissue and not on the source of the organ or tissue. For example, organs in ex vivo testing can be assessed for suitability for substance testing by acting as their own controls, whereby exogenous or endogenous controls, depending on the specific process(es) being tested, e.g., absorption, transport, metabolism, efficacy and/or safety/toxicity, can be added before, during and/or after a test substance and/or endogenous components can be quantitatively monitored before, during and/or after perfusion. In this way, instead of reflecting individual source variability, data generated on the fates and effects of substances on the same type of organ from different donors can be normalized.

Assessment of each organ or tissue for suitability for substance testing can occur at one or more stages. For example, suitability can be determined after procurement, cold storage and/or normothermic reperfusion of the organ or tissue, but prior to dosing the test substance. Alternatively, or additionally, suitability can be determined before, during or after testing of the substance. In this testing, at least one exogenous control may be added and/or at least one endogenous function or component may be quantitatively monitored before, during and/or after perfusion with the test substance. In this way, suitability of the organ or tissue for use in the testing may be ensured. In addition, the data generated on the fates and effects of test substances on the same organ or tissue from different donors may thereby be normalized for source-generated variability.

Each type of organ or tissue can be assessed for suitability for testing. Assessment can be in terms of its physiology, wherein one or more endogenous function is determined by evaluating, for example, perfusate flow, vascular resistance, gaseous exchange, electrolyte balance and organ function, such as motility (intestine), bile secretion (liver), urine production (kidney), respiratory compliance/resistance (lungs) and the mechanics of heart contraction (heart).

In addition, each organ or tissue can be assessed for ischemic and/or reperfusion injury by, for example, exogenous methods, such as Raman spectroscopy or Maldi mass spectroscopy of the perfusate, excretory fluid(s) and/or the organ or tissue.

The choice of controls (also referred to as "normalizing standards," "validation standards" and "validation controls") can vary for the same organ or tissue depending on the specific process(es) under investigation, e.g., absorption, transport, metabolism, efficacy or safety/toxicity, etc. A key factor is that the standards do not interfere with the evaluation of the properties, fates and effects of the test substances under evaluation. The table below lists exemplary validation standards and methods.

| Perfused Organ | Investigative Process | Validation Standards and Methods |
| --- | --- | --- |
| Intestine | Passive Absorption | Antipyrine, Terbutaline, Mannitol, Radioactively and/or Fluorescently Labeled and Unlabeled Dextrans |
|  | Active Absorption | Cephalexin, Arginine |
|  | Bio-signatures of Toxicity | Raman Spectroscopy |
|  | Post Translational Modifications | Maldi Mass Spectroscopy |
|  | Phase I Metabolism | Phenacetin (CYP1A2) Tolbutamide (CYP1C9) S-methenyltoin (CYP2C19) Dextromethorphan (CYP206) Chloroxazone (CYP2E1) methadone (CYP3A4) |
|  | Phase II Metabolism | Harmol, Naphthol |
| Liver | Plasma Clearance | Propanolol, Atenolol |
|  | Biliary Excretion | Tetrabromosulphophthalein, Dibromosulphophthalein, Indocyanine Green, Bile Salts |
|  | Receptor-Mediated Endocytosis | Asiologlycoproteins |
|  | Phase I Metabolism | Phenacetin (CYP1A2) Tolbutamide (CYP1C9) S-methenyltoin (CYP2C19) Dextromethorphan (CYP206) Chloroxazone (CYP2E1) methadone (CYP3A4) Carbamazepine 7-Nitrazepam |
|  | Phase II Metabolism | Harmol, Naphthol |
|  | Bio-signatures of Toxicity | Raman Spectroscopy |
|  | Post Translational Modifications | Maldi Mass Spectroscopy |
| Lung | Absorption via Airways | Salbutamol, Ipratropium |
|  | Active Uptake | Putrescine, Spermine, Spermidine |

-continued

| Perfused Organ | Investigative Process | Validation Standards and Methods |
| --- | --- | --- |
|  | Phase I Metabolism | Phenacetin (CYP1A2) Tolbutamide (CYP1C9) S-methenyltoin (CYP2C19) Dextromethorphan (CYP206) Chloroxazone (CYP2E1) methadone (CYP2A4) Carbamazepine |
|  | Phase II Metabolism | Harmol, Naphthol |
|  | Biosignatures of Toxicity | Raman Spectroscopy |
|  | Post Translational Modifications | Maldi Mass Spectroscopy |
| Kidney | Glomerular Filtration | Inulin, Creatinine |
|  | Active Secretion | p-Aminohippuric Acid |
|  | Active Reabsorption | Tetra-ethylammonium Acetate, Sodium, Glucose |
|  | Phase I Metabolism | Phenacetin (CYP1A2) Tolbutamide (CYP1C9) S-methenyltoin (CYP2C19) Dextromethorphan (CYP206) Chloroxazone (CYP2E1) methadone (CYP2A4) |
|  | Phase II Metabolism | Harmol, Naphthol |
|  | Phase III Metabolism | Mercaptans, Glutathione Conjugates |
|  | Biosignatures of Toxicity | Raman Spectroscopy |
|  | Post Translational Modifications | Maldi Mass Spectroscopy |
| Heart | Uptake | Dopa, Dopamine |
|  | QT Interval | Electrophysiology |
|  | Bio-signatures of Toxicity | Raman Spectroscopy |

In the validation stage, the organ or tissue is assessed for suitability for testing of one or more parameters relating to the test substance, before, during and/or after administration of the test substance. Preferably, the same perfusate is used with at least one control substance having a known qualitative or quantitative effect with respect to the parameter being assessed with respect to the test substance, and the same parameter is assessed with respect to the control substance or substances. If the control substance competes with the test substance, it is generally preferred, although not always necessary, that the control substance be perfused through the organ or tissue after the test substance has been perfused through the organ or tissue. In this way, it can be determined whether the organ or tissue is still having its effect, or being affected by, substances in connection with the same parameter as is being considered for the test substance. For example, for active or passive absorption, it can be determined even with a competitive control that the absorption process is still taking place in the organ or tissue. Use of potentially competitive control substances can also provide information regarding what mechanism is involved with respect to the test substance. For example, different control substances listed for active absorption listed above utilize different mechanisms. Thus, the presence or absence of actual competition can allow one to identify the mechanism involved.

When the control substance does not compete with the test substance, it is less significant whether the control substance is perfused through the organ or tissue before, during or after the test substance. However, it is generally preferred that perfusion with the control substance occur during and/or after perfusion with the test substance to ensure that the parameter being tested is not inappropriately affected by some extraneous change in the organ or tissue during the course of the testing with the test substance.

In addition, by comparing known rates of, e.g., absorption by the organ or tissue of the control substances, a ratio of the rate of such absorption of the test substance to that of the known control substances can be determined. Such a ratio permits normalization between organs. For example, even though different organs, which have undergone different degrees of injury, disease or other degradation, should generally have the same ratio of absorption between a given test substance and a given standard control or set of control substances. Thus, if that ratio (within reasonable limits) is not seen in tests using a plurality of organs, it may be determined that one or more of the organs has undergone such degradation that its results are not useful. In this context, it is often desirable to use a plurality of control substances that have known but significantly different values for the parameter being tested. Using such controls, it is possible to quantitatively assess the effects of the test substance relative to the controls, regardless of the state of the particular organ in which the test is carried out, unless the entire functionality of the organ relative to the parameter being tested is no longer present.

As another example, where active absorption is being tested, use of a control substance with zero or nearly zero normal active absorption and a second control substance with substantial normal active absorption can show whether the active absorption values obtained with the test substance are reliable. For example, if the test substance is absorbed, but the normally non-absorbed control substance is also absorbed, it may be that the absorption being observed is a passive absorption that is not related to the normal active absorption being tested for. Similarly, if the normally highly actively absorbed control substance is not absorbed, it would be apparent that the organ's active absorption mechanism has been degraded to such an extent that whether or not the test substance is absorbed, it is known that the results are not likely to be valid.

Exposing a substance to metabolically active extracorporeal organs or tissues according to methods disclosed herein generates data and information. Such data and information may be stored on any computer-readable medium and/or in any other suitable form. Such data and information may be considered a transferable information product.

In aspects, the disclosed methods may generate data and information about a substance. As used herein, a substance can include any product or component thereof. In particular, the substance can include a compound of interest in the development of a product such as a pharmaceutical product. Data or information about the substance may include characteristics of the substance itself, its derivatives, metabolites and/or other related substances.

Data or information obtained about the substance may include the effects of the substance on ex vivo organs or tissues, the effects of ex vivo organs or tissues on the substance and the effects of the substance on other substances exposed to the ex vivo organs or tissues. Information about the substance and its effects may include, but is not limited to, organ or tissue absorption, transport, metabolism, induction, repression, elimination, pharmacokinetics and bioavailability, toxicity, efficacy, metabolites, metabolite pharmacokinetics, metabolite toxicity, metabolite efficacy, interactions with other substances, and other reactions and products of those reactions for assessing usefulness or other characteristics of the substances or the metabolites or derivatives thereof.

Embodiments include business methods and models of using features of the present invention to improve drug development, reduce costs and/or generate revenue. For example, the methods can include making available to a third party a service including conducting testing as part of a drug development program. Embodiments include making available to a third party the resulting data and/or information generated from that testing in the form of an information product. The service and product may be made available to a third party for a fee. It should be appreciated that a fee may include a fixed amount or lump sum, an amount that is based on a variable, such as a percentage of the profits of the sale of a product, or any other suitable form of remuneration, compensation or reimbursement. Accordingly, an entity that conducts testing according to the disclosed methods and generates data and information from the disclosed methods, referred to herein as a provider, may generate revenue from marketing and selling services and products described herein to third parties.

In another aspect, disclosed methods may generate data and information about the ex vivo organ or tissue exposed to the substance. In applications of disclosed methods, testing results may provide data and information on classes of compounds, receptors, biochemical pathways, physiological and pathological mechanisms, biomarkers and other phenomena associated with living organisms. Accumulated data and information generated in performing disclosed methods may create a resource of statistically significant and scientifically valid information. Each of these forms of data and information constitutes a transferable information product.

In embodiments, an information product provided to a third party may include raw data generated from performing disclosed methods. Alternatively, or in addition, an information product provided to a third party may include an interpretation or evaluation of raw data in various levels of useful and/or conclusory forms. Raw data may be retained as proprietary by the provider, and only information derived from the raw data may be made available as an information product to the third party. Therefore, in addition to the service of conducting the testing according to disclosed methods and generating raw data, a provider may interpret data for a third party.

Data or information about a substance derived from performing at least one of the disclosed methods may be used in numerous ways, thereby conveying value to the information product. Data or information may, for example, be used to determine whether the substance has a potential beneficial use, whether the substance has potential to be used for a particular purpose, or to what degree the substance has potential to be used for a particular purpose. For example, data collected from exposing a substance to a metabolically active extracorporeal tissue or organ according to disclosed methods may be used to determine if the substance should undergo further testing to determine its usefulness as a pharmaceutical product. To this end, data and information may be used to eliminate non-useful substances from a population or pool or group of substances. It should be appreciated that determining that a substance is not useful for a particular candidate application is of significant value allowing allocation of resources to further the development of those substances that are identified as being potentially useful, for example.

An information product may be used by a third party such as a drug developer involved in the development of products such as pharmaceuticals. The drug developer may supply one or more substances to the provider for testing. The substances supplied to the provider may be substances identified at any stage of the drug development process including after the drug has been developed. The drug development process typically includes a series of steps, stages or phases associated with different levels of testing. The phases can include the discovery phase, pre-clinical phase, the clinical phases and the post-approval and post-marketing phases. At each phase in the development process, a drug developer incurs significant cost for each substance carried forward to the next phase. Included in the cost to the drug developer are direct expenses associated with conducting testing. For example, by the time a substance has advanced through the pre-clinical phase of testing, a substantial amount of money has been spent on that substance. By phase IIb, a drug developer has already spent usually more than three years in clinical trials and typically nearly $40 million testing the compound in humans.

In addition, there are indirect costs associated with delays in advancing beneficial compounds to market. Problems such as conflicting data, uncertainty about results, and unexpected problems all require additional testing during which sales, including peak sales, of the drug could have occurred. There are also indirect costs associated with decreased yield from profits on the sale of compounds not developed. In other words, for every efficacious and safe drug that is not developed, for every day a drug remains off the market, for every additional test that must be performed on a compound, there is a cost to the drug developer.

Information products of disclosed methods may provide definitive, relevant, organ-specific, species-specific data to address problems which can occur during each of the phases of research and development. Information products of disclosed methods may guide drug candidate selection, facilitate problem-solving such as discrepancies in data or information obtained from other types of testing, and may expedite regulatory approval throughout development and compliance processes and for regulatory compliance.

Information products may create value and efficiency in the drug research and development process in at least four ways. First, information products may increase the number of substances that can be used and sold as pharmaceutical products by potentially providing more and better data earlier in the research and development process. Second, information products may increase the days of peak sales by potentially shortening the time necessary to advance products to market. Third, information products may reduce development costs by avoiding returns to earlier phases due to unexpected problems later in the process, as well as potentially reducing the overall time to market. Fourth, information products may contribute to protecting humans from toxic side effects during clinical testing of substances in the development process and during use of the released substance.

In the discovery phase, substances are synthesized and purified for screening and testing at the sub-cellular and cellular levels to identify those substances with potential beneficial uses. Screening methods during the discovery phase can include high-throughput testing using combinatorial chemistry to create and test numerous different molecules. Other screening methods can include chemical genomics and bioinformatics. Chemical genomics rapidly characterizes a large pool of small molecules against target cells or tissues. Bioinformatics, or in silico biology, is used to gather gene and protein sequence data from different life forms to compare potential treatments, known gene function and biologically active binding sites through computer analysis to identify similarities or patterns. Information products of the invention may dramatically increase the pool of potentially useful compounds at the discovery phase of the research and development pipeline. In the discovery phase, information products may resolve problems such as conflicting data from high-throughput testing which may be poorly predictive of efficacy. In addition, by offering the prospect of less extrapolation and more comprehensive screening of target compounds than existing in silico models, information products and in silico models generated therefrom may allow a drug developer to much more accurately target compounds in the early stages of discovery.

Potentially useful compounds synthesized, purified and preliminarily screened for potential usefulness in the discovery phase may enter the pre-clinical phase. The pre-clinical phase typically includes testing of substances in in vitro models using cells and tissue slices and in animals to determine information about the substances and their effects.

Information products of the disclosed methods enable the drug developer to identify the most-promising compounds and to reconcile or resolve discrepancies in data or information obtained from other types of testing. Animal models employed in the pre-clinical phase of drug development can be imperfect models for how a substance actually acts and is acted upon in a human. For popular therapeutic areas such as oncology and neurology, animal models are particularly misrepresentative of humans, as evidenced by the high attrition of substances directed to those therapies through the clinical phases. As a result of animal and in vitro testing often being poorly representative of humans, the research and development process frequently does not identify the best lead compounds from a family of compounds in the early stages of development.

Information products of disclosed methods may provide value to the drug developer by minimizing delays in the development of a drug and shortening the period of time required to release a drug, thereby increasing the days of peak sales of the developed drug. To this end, earlier identification by disclosed methods reduces the risk of being beaten to market by a competitor and provides the drug more time under patent protection, resulting in additional peak sales. If a drug which will ultimately have annual peak sales of $580 million, for example, must be returned to pre-clinical testing due to unexpected problems such as unexpected metabolites unable to be predicted in pre-clinical animal studies but that emerge in human clinical trials, the cost to the drug developer for every month of delay is significant. Information products, therefore, minimize or eliminate delays associated with uncertainties caused by unsuccessful animal-to-human extrapolation and maximize the value of peak sales of the drug.

Additionally, animal studies often yield conflicting data across species. Indeed, in the pre-clinical phase of drug development, common problems include false negatives and false positives, conflicting absorption, toxicity, or efficacy data across animal species and uncertainty about rank order within families of compounds.

Information products of disclosed methods may provide data or information about a substance and its effects that is not available from other types of testing and, in some cases obviates the need for other types of testing. Information products may improve the correlation between data obtained in the pre-clinical stage and data obtained in the clinical stage of drug development. Therefore, in the pre-clinical phase, information products may minimize and/or resolve conflicting absorption and uptake data across species, conflicting toxicity data across species, uncertainty about absorption and uptake rank order, uncertainty about efficacy rank order, uncertainty about PK-toxicity relationship rank order, uncertainty about drug-drug interaction with specific drugs and rank order and conflicting efficacy data across species. It should be appreciated that distinguishing less-promising compounds from more promising compounds at this stage or earlier in the process saves the delay and cost to the drug developer of further testing compounds with minimal potential. This allows the drug developer to allocate more resources toward the more promising compounds to advance them efficiently through the later stages of the development process and minimize, if not avoid, bringing toxic compounds into clinical trials. Information products may also be used to select appropriate patients for clinical trials based on parameters of the test substance, sensitivity to the substance or any other suitable factor. In addition, information products may be used to select which of a group of different formulations including the same or different compounds should be used in clinical trials.

Potentially useful substances found to have desirable safety and efficacy characteristics in various animal models may enter the human clinical phase of drug development. The clinical phase includes at least four phases: phase I, phase IIa, phase IIb and phase III. Phase I testing involves the initial introduction of the potentially useful substance into a human clinical test subject. Phase I testing is used to determine characteristics of the substance in humans, such as its metabolism, structure-activity relationships, mechanism of action and other pharmacokinetic and pharmacological data. In addition, phase I testing provides metabolic and pharmacologic actions and side effects of the substance in humans. Phase I studies may further determine if the substance can be used as a research tool to study biological phenomena or disease processes or to further define the testing to be performed during phase II. In phase I clinical testing, common problems include the emergence of unexpected metabolites and unexpected problems with bioavailability due to low absorption and/or high metabolism. Such problems indicate that animal studies conducted in pre-clinical testing were not sufficiently representative of human conditions to adequately predict problems encountered in humans. Therefore, information products of disclosed methods provide a drug developer a tool to further test the compounds in an environment more representative of the human condition without further risk to the life or well-being of clinical test subjects. Furthermore, the contribution of an individual organ to the fate and effects of substances can be quantified in information products.

Application of information products to problems encountered in the pre-clinical phase and phase I for substances in high-potential therapeutic areas is especially effective and has the potential to fundamentally improve the pharmaceutical research and development process. Accordingly, information products of disclosed methods provide great values in early stages of drug development such as in pre-clinical and phase I clinical stages of development. Information products of disclosed methods may be particularly designed to resolve problems arising in the pre-clinical phase and phase I including conflicting absorption, toxicity, and/or efficacy data across animal species, uncertainty about rank order within a family of compounds related to absorption, efficacy, and PK-toxicity relationship, and uncertainty about drug-drug interactions in the pre-clinical phase and unexpected problems with bioavailability and uncertainty about surprise metabolites in phase I or later.

Phase II testing is performed in a larger population of clinical test subjects than phase I in order to generate preliminary data on the effectiveness of the drug for a particular indication or indications in individuals with such a disease or condition. In addition, phase II testing can provide information on short-term toxicity and side effects of the substance. Common problems in phase II of clinical testing include uncertainty about magnitude of therapeutic effect for estimation of the number of test subjects, and uncertainty about correct inclusion/exclusion criteria based on drug-drug interaction. If a substance demonstrates favorable characteristics based on phase II studies, e.g., effectiveness with minimal or tolerable side effects, the substance may proceed to phase III human clinical testing. Phase III clinical testing enables the drug developer to expand the data of the efficacy and toxicity of the drug to fully assess the risk-benefit relationship of the use of the drug in humans. Phase III also provides a basis for extrapolating the data and findings in relatively small populations of test subjects exposed to the substance to a broad population of subjects who may benefit from use of the substance. At each of these late-stage clinical phases, an information product may, for example, be further used by a drug developer to resolve any issues associated with efficacy, unexpected side effects, toxicity, and uncertainty about drug-drug interactions. Even after a drug has been made available to the public, typically referred to as phase IV, long-term follow-up testing may be required to confirm continued usefulness of the drug, long-term toxicity or in product line extension development which can be addressed using the information product. This further testing may be performed in accordance with regulatory compliance.

Late-stage failures of substances occur, in large part, because of the limited ability of existing methods, such as animal testing in the pre-clinical phase, to conclusively predict efficacy and toxicity in humans. In fact, significant attrition of substances occurs in late clinical stages of drug development, primarily in phases IIb and III, indicating that substances are failing to be identified earlier for lacking efficacy (phase III) and for having intolerable levels of toxicity (phase II) in humans. By phase IIb, a typical drug developer has, on average, already spent more than three years in clinical trials and nearly $40 million on testing the substances in humans, a significant loss to any size drug developer. Pursuit of these substances by drug developers often occurs at the expense of pursuing other substances.

Furthermore, investors and analysts tend to follow substances in the later stages of the development process. More specifically, analysts evaluate pharmaceutical research and development almost exclusively on the number of substances under regulatory review, up for filing with a regulatory body, and in, or entering, phase III. To this end, information products of disclosed methods may be used by both small and large pharmaceutical companies to reduce risks associated with missed opportunities of developing a promising drug by choosing the wrong substance and to identify the right substance sooner allowing the drug developer to capture additional peak sales. Enabling the development of substances that would otherwise have not been brought forward is particularly valuable to small pharmaceutical companies which may not have the resources to cycle back and test multiple back-up substances. In addition, both large and small companies alike can benefit from additional peak sale profits from time savings made possible by information products of disclosed methods. Accordingly, by increasing the probability of identifying high numbers of useful substances, and by limiting the number of late-stage failures and unexpected late-stage delays, particularly in phase III, information products provide drug developers important intangible benefits, such as strengthened public trust, investor credibility, and stock market performance, in addition to predicted research and development productivity gains.

In addition to reducing costs preventing further investment in unqualified drugs and resolving conflicting or uncertain data directly impacting the cost of developing a drug, information products of disclosed methods may also contribute to identifying useful products and components thereof. The expected value of substances that would otherwise be abandoned and that are enabled by information products of disclosed methods to move forward in the development process can be significant. The expected value attributed to the application of information products that leads to an approved substance may be based on profits from the substance, additional peak sales from reduced approval time, and cost savings from reducing the number and duplication of tests that are accrued through the development process.

In addition to applying information products of disclosed methods to specific problems in particular phases of drug development, information products may be applied to particular therapeutic areas of drug development. Information products of disclosed methods may impact those therapeutic areas where existing tools, such as animal and in vitro models, are particularly non-predictive and/or where the sales of drugs that are launched are expected to be high. The expected impact of information products of disclosed methods on a particular therapeutic area can be based on, for example, the failure rate from phase I to drug launch, projected sales growth indicating future potential of the therapeutic area, and average sales per high-potential drug indicating the extent of high-potential drugs within a therapeutic area. The failure rate during the clinical phase of drug development reflects the tendency within a therapeutic area to choose the wrong compounds from a family of compounds during the pre-clinical phase of drug development due to animal and in vitro testing being poorly representative of humans.

Information products of disclosed methods may have particular potential relevance and value for "proof of concept" studies, which tend to be organ-specific, and efficacy studies in therapeutic areas for which treatment and testing is organ-specific. In addition to therapeutic areas such as musculoskeletal, inflammatory, gastrointestinal, central nervous system, and vaccines, organ-specific therapeutic areas may include, for example, respiratory, infectious diseases, diabetes/metabolic, oncology, and cardiovascular. For example, disclosed methods may be applied to drug development in the area of oncology where in vitro cancer models are often unable to mimic adequately the architectural and cellular complexity of real tumors. In fact, nine out of every ten attempts to bring a cancer drug to market typically fail. Also, while the extent of high-potential drugs in oncology is smaller than that of its peer therapeutic areas above, oncology is becoming increasingly attractive from a drug sales perspective. Therefore, information products of disclosed methods applied to a therapeutic area where existing tools are particularly non-predictive, but where the sales of drugs that are launched are expected to be high, confer substantial value.

Information products may be used to fulfill requirements to comply with regulations such as governmental regulations, for example, in an approval process or after a substance has been approved for a particular use. At various stages of the drug development process, governmental or other regulatory bodies may require submission of information obtained about a substance. For example, in the United States, the Food and Drug Administration (FDA) reviews the results of laboratory animal and human clinical testing performed by companies to determine if the product intended to be marketed is safe and effective. At the pre-clinical stage, for example, the regulatory body may conduct a safety review of a potentially useful substance in the form of an investigational new drug application filed with the FDA. Once sufficient data from phase III clinical studies of a substance has been obtained, the studies can be used to file a new drug application with the FDA in accordance with regulations and requirements for marketing the substance as a drug. Even after a single substance is identified and marketed, post-marketing clinical and non-clinical studies along with post-marketing surveillance may be required. To this end, medical, chemical, pharmacological, toxicological, and/or statistical data and other relevant information may be reviewed to determine if further development of the substance should proceed. Accordingly, information products of disclosed methods may constitute information necessary for compliance with regulations by a third party and may be made available to the third party for a fee.

In addition to enhancing the drug development process and providing value to a third party, a provider may create a resource of information based on accumulated data and information generated by the disclosed information. This data and information may include, but is not limited to, information on classes of compounds, receptors, biochemical pathways, physiological mechanisms, and other scientifically valid conclusions. This information may be used to enhance understanding in areas related to or different from drug development. Information products may be in the form of access to this resource of information made available to a third party for a fee. Such information may be used to compare effects in various types of organs and tissues to formulate patterns and models of predictability of those effects. Information products may be used to compare information about the substance and its effects in different organs and tissues, in different species, and in different conditions of organs and tissues such as normal, abnormal, diseased or damaged organs and tissues.

Information products may further be used to formulate models based on statistically significant and scientifically valid data and information accumulated from repeated testing using disclosed methods. In particular, information products may be used to create an in silico model of the effectiveness of a tested compound.

Currently, using advanced computer methods, the effectiveness of drugs and drug candidates can be modeled in silico ("biosimulation") during the early stages of drug development, e.g., during drug discovery, by matching the physical/chemical properties of a compound with various biological events. However, these current methods are limited because most in silico models are built from in vitro data, where the nature of biochemical assays often does not reflect the complexity of the intact human organs or organism. For example, an in vitro-based model may simulate a compound's interaction with one or two pathways, when in reality, the compound also uses several other pathways that are not accounted for in modeling programs informed only by in vitro acquired data. As a result, these in silico models have the same limitations in terms of predictive power as conventional in vitro testing.

Embodiments of the invention provide methods for producing information products that correlate structural, physical and/or chemical characteristics and properties of substances with their fates and/or effects on absorption, transport, metabolism, and/or elimination of the substance, or toxicity thereof. These data are advantageous and an improvement over more conventional in vitro-based methodologies because they more accurately match the in vivo environment, and, more preferably the human in vivo environment, compared with in vitro or non-human animal data. Thus, methods provided herein can produce more accurate in silico models, reducing limitations currently constraining the effectiveness of existing models. For example, significantly less extrapolation from experimental results to expected effects in vivo would be needed. In addition, methods of the invention can be used to evaluate target hits from in vitro-based in silico models, which could then be screened for physiochemical and pharmacokinetic properties. Embodiments of this aspect of the inventive methods can provide more accurate selection of promising pharmaceutical candidates in the earliest stages of discovery for further screening and development. Moreover, ex vivo methods provided herein using intact human organs provide genomic and proteomic analytical screens to identify biomarkers of human disease, toxicity and other pharmacologic activity, as well as time-dependent changes in enzymes and proteins (proteomics) in perfusate secretions and biopsies from metabolically-active isolated perfused human organs or tissues under physiologic conditions.

Accordingly, information products may include data needed to formulate an in silico model and may be made available to a third party for a fee. Alternatively, information products may include in silico models developed by the provider and may be made available to a third party for a fee.

Application of disclosed methods to generate information products may be tailored to individual needs of a company. To this end, an evaluation of the drugs under development by a drug developer, such as a pharmaceutical company, may be conducted. The evaluation may further include an effect information products may have on the drug development process of the third party. In this regard, the evaluation may be a prospective evaluation. In addition, or alternatively, the evaluation may include an effect of information products on the drug development process of a third party. In this regard, the evaluation may be a retrospective evaluation. An evaluation may be performed at any suitable stage of the drug development process or the life of the drug on the market to determine the effect or the potential effect of the information product on drug development and use.

An evaluation may be conducted in order to market information products. In this regard, a provider may make available to a third party an evaluation that includes an economic effect of an information product on the drug development process. Alternatively, an evaluation may be conducted for any other suitable purpose. An evaluation may be conducted for a fee in addition to, or, alternatively, included in, any of the fees discussed herein or combinations thereof.

More specifically, an evaluation may include determining where and in what situations a drug developer is expected to extract the most value from employing an information product of a disclosed method. Assessing the impact of disclosed methods on specific problems in each phase of the research and development process contributes to this determination. Additionally, a comparative analysis of different scenarios and assumptions at large versus small companies may suggest differences in the potential sources of value for each, based on differences in their research and development processes and resources. Such an evaluation may take into consideration the percentage of the company's pre-clinical research programs that are in therapeutic areas where information products of disclosed methods may be expected to generate meaningful efficacy data. In addition, an evaluation may reveal where there is an opportunity to leverage the ability of information products of disclosed methods to resolve conflicting species data as a way to increase or reverse a declining trend in the number of investigational new drug applications. An evaluation may also determine the number and type of studies that may provide the most benefit to the company. This evaluation may be based on the average number of compounds brought forward each year from pre-clinical into phase I. Moreover, the evaluation may reveal unexpected problems with bioavailability and toxicity that information products of disclosed methods may resolve based on the number of phase I compounds that have been in the phase longer than the industry average.

The evaluation may estimate the total value of the successful application of an information product of a disclosed method. The total maximum value of the information product may include values associated with yield, time, and cost. Yield may, for example, be measured by profits from launched or fully developed incremental compounds that would not have been uncovered and brought forward without the information product. Time may be measured in terms of additional peak sales realized from resolving the problem or situation more quickly by using the information product. Cost may be related to decreased expenses associated with reducing the amount of testing such as the number of trials and/or the number of repeated trials. The values of yield, time and cost can, therefore, be summed to determine the total maximum value of the information product. The expected value takes into account probabilities associated with the likelihood that the total maximum value of the information product will be realized.

The evaluation may estimate the total value of the successful application of an information product of a disclosed method against a range of common problems such as problems associated with each stage of drug development. The problems may include conflicting data from high throughput testing in the discovery phase; uncertainty about efficacy rank order, conflicting absorption and uptake data across species, conflicting toxicity data across species, conflicting efficacy data across species, uncertainty about PK-toxicity relationship rank order, uncertainty about drug-drug interaction rank order, and uncertainty about absorption, and uptake rank order in the pre-clinical phase; unexpected problems with bioavailability due to low absorption and/or high metabolism and uncertainty about appearance of surprise metabolites in phase I; unexpected problems with PKIPD (pharmacokinetic divided by pharmacodynamic) due to species differences, differences between healthy volunteers and diseased patients, difficulty getting enough subjects for trials, uncertainty about magnitude of therapeutic effect for estimation of sample size, and uncertainty about correct inclusion/exclusion criteria in phase II; and uncertainty about correct inclusion/exclusion criteria in phase III. In each situation or problem encountered in the development process of a drug the expected value of the information product may result in additional compounds that would not have otherwise been pursued, additional profits due to time savings and firm cost savings associated with a decreased amount of required testing. The expected value of the information product can be expected to derive from at least one of these sources and other sources.

For each situation or problem that arises during the development process, one can determine a total maximum value and an estimated expected value of the effect of the information product on resolving the problem. If, for example, a problem arises in the development of a drug that requires a drug developer to place the compound on hold to resolve the problem, the delay to resolve the problem may result in a loss of peak sales, for example. The total maximum value includes the value the information product confers to the drug developer in resolving the problem. The probability of the problem occurring coupled with the probability that the total maximum value of the information product will be achieved can be used to determine a total value. This relationship between expected value and total maximum value may apply to each situation or problem.

Methods of calculating the expected value of an information product in a particular scenario may include determining a suitable value equation for each situation or problem to which the information product is applied. The value equation may include the total maximum value of the information product.

Determining the expected value of an information product may also include quantifying different base-case assumptions to determine the values of yield time and cost. The evaluation may assume values for parameters such as yields by development phase, duration of each development phase, direct costs by development phase, expected launch year from end of phase, average peak sales per year and years of peak sales. The evaluation may also include values for annual peak sales per launched product, e.g., drug, and/or projected launched products. The evaluation may further include an estimated reasonable discount rate. The assumptions may be determined based on market data from academic articles, web resources, industry interviews or any other reliable source of information.

Methods of evaluation of an information product may include building generic decision trees for each problem or situation encountered in the development process or in a portion of the process. For each situation, a unique decision tree that maps the possible paths of using the information product may be produced. For example, a decision tree for resolving conflicting toxicity data across species as typically encountered in the pre-clinical phase of drug development may be produced. The decision tree may include any number of branches indicating the possible permutations of results that may occur in attempting to resolve the situation. The decision tree may include, for example, a branch for whether additional animal testing will resolve the conflicting toxicity data. If animal testing does not resolve the problem, a decision branch may include whether the information product of a disclosed method resolves the problem. If the information product resolves the problem, a decision branch may include whether the information product includes results that are favorable based on intrinsic properties of the compound, e.g., acceptable toxicity levels. If the information product includes results that are favorable, the decision tree may further include a branch for whether there are any remaining issues that must be resolved that would prevent the compound from moving forward in the development process.

Methods of evaluation of an information product may also include determining and assigning probabilities to each possible result that may occur in each branch of the decision tree. The probabilities at the branches of the decision tree may be based on market data from academic articles, web resources, industry interviews, accumulated data generated from and experience with the disclosed methods and any other reliable source of information. For example, it can be assumed that there is only a 50% probability that additional animal testing will resolve conflicting toxicity data across species and that, if an information product of a disclosed method is applied, the probability of resolving the conflicting data increases to 80%. It can further be assumed that there is a 40% probability that testing using a disclosed method results in a compound having favorable characteristics, i.e., acceptable toxicity levels, and that there is a 20% probability that no other testing needs to be performed to allow the compound to move forward in the development process.

The expected value contributed by an information product may be derived by calculating the total maximum value in terms of yield, time and cost parameters for each situation or tree. The expected value may be calculated based on the probabilities that application of an information product to the problem results in a successful product, e.g., drug, launch. Returning to the example above, if the total maximum value of employing an information product to resolve conflicting toxicity data is $305 million based on the yield, time and cost values, the expected value of the information product may be calculated to $9.7 million for a single compound, taking into account the probabilities associated with each possible result in resolving the problem ($305 million×50%×80%×40%×20%). Therefore, the information product provides value to a drug developer in resolving problems with particular compounds that are enabled to be developed and released. Information products of disclosed methods offer a potential resource to guard against delays associated with re-testing the compounds. The application of such information products may create an opportunity for loss avoidance against the loss in total maximum value of the product.

Perfusion Examples

The nature of the perfusate is preferably adapted to the particular tissue, organ or combination thereof to be tested, or to the chemical or other characteristics of the test compound. Those skilled in the art can select appropriate solutions. However, it is preferable in the present invention that a single base perfusate be used throughout the suitability testing, substance testing and/or control administration and monitoring to control for potential perfusate-driven variation.

For perfusions under normothermic conditions, the perfusate preferably comprises: water, sodium, potassium, calcium, magnesium, chloride, buffer component (containing bicarbonate ions and TES, MOPS or BES, for example), glucose, glycerol, choline, amino acid component (such as glutamate, aspartate and/or glutamine), co-enzyme (such as thiamine cocarboxylase), vitaminoid (such as carnitine) and proteins (such as human albumin and insulin). Alternatively, human blood plasma can be used.

A preferred perfusate used in normothermic conditions, such as RS1 (AQIX®, London, England) or OPB-1 or OPB-2 (Organ Recovery Systems, Inc., Des Plaines, Ill.), has a pH ranging from about 7.13 to about 7.41 and an osmolality of about 286 mOsm and comprises the following components:

| OPB-1 Components | OPB-1 Concentrations (mM) |
| --- | --- |
| Organic acids | 5 |
| Chloride | 116.4 |
| Sodium | 135 |
| Calcium (ionized) | 1.2 |
| Potassium | 5 |
| Bicarbonate ions | 25 |
| Glucose | 10 |
| TPP (cocarboxylase) | 0.04 |
| Magnesium (ionized) | 0.45 |
| Glutamine | 0.4 |
| Glutamate | 0.3 |
| Glycerol | 0.11 |
| Carnitine | 0.05 |
| Sterile water | n/a |
| Aspartate | 0.02 |
| Choline | 0.01 |
| Protein (Insulin) | 0.002 (25.00 mIU) |
| Human serum albumin | 6% |
| Buffer (BES) | n/a |

Additionally, perfusates can be modified for use with certain organs, as described in the following table by way of example.

| Organ | Added Perfusate Component |
| --- | --- |
| Liver | N-acetylcysteine |
|  | ATP |
|  | Dibutylcyclic AMP |
|  | Superoxide dismutase |
|  | Glycocholic acid |
|  | Glycochenodeoxycholic acid |
|  | $^3$H-mannitol |
| Intestine | Noradrenaline |
|  | Dexamethasone |

-continued

| Organ | Added Perfusate Component |
|---|---|
| Kidney | Methionine |
| | Alanine |
| | Glycine |
| | Serine |
| | Proline |
| | Isoleucine |
| | Mannitol |
| | Creatinine |
| | N-acetylcysteine |
| | ATP |
| | Dibutylcyclic AMP |

Perfusion Study Reports

If a report of the perfusion study results is to be provided to a third party or simply retained, the report can be in draft or final form and contain study information and data including some or all of, but not limited to: description of the experimental procedures including, for example, the perfusion method and preparation details; organ or tissue weight at the start and end of the perfusion study; mass balance data of, for example, radioisotopes in perfusate, plasma, tissue or organ, and/or bodily fluids, such as bile, as applicable; plasma and/or organ or tissue clearance; standards (also termed "controls"), control methodologies and substances; excretion of conjugated and unconjugated standards and any applicable conjugates; rate of formation of metabolites of standards and other facets of the metabolic profiles of standards; description of standards, including, for example, metabolic profiles; physiological flow rates at each collection timepoint, e.g., bile, arterial, etc., as applicable; organ donor details and medical records (as permitted); test compound data sheets; test compound receipts and usage records; dosing records; sample collection records; sample weight records; sample storage and shipment records; location of study site; any additional measurements and/or analyses performed during the study or otherwise related to the study; and/or any reports and/or data supplied by a contract facility.

Set forth below are illustrative assays employing embodiments of methods of the invention. This disclosure is of a general nature and the non-limiting protocols below provide embodiments of the general disclosure.

Perfused Intestine Protocol Example

The ability to generate unequivocal data regarding the absorption of substances in the human intestine is important in decisions regarding the use of substances that might be ingested, such as in drug development, especially prior to clinical trials Such data can be generated using isolated intestinal segments because: (a) the substances are presented via the intestinal lumen as in vivo; (b) the barriers between the intestinal lumen and blood are present and intact; and (c) the composition and flow characteristics of the perfusate mimic those in vivo.

Perfusion Conditions

Approximately three liters of perfusate are used per analysis. The perfilsate preferably comprises matched human erythrocytes (preferably, previously washed) suspended in a buffer (at about 15 to about 20% (v/v)) comprising 4-6% human serum albumin, at a pH of preferably about 7.4.

Preferably, the perfusate is passed through a blood transfusion filter, followed by a leukocyte-removing filter, heparin is added and the pH adjusted, if necessary, to, preferably, about 7.4. The perfusate is preferably stored at room temperature until added to the perfusion apparatus. An aliquot of the surplus perfusate can be centrifuged (at about 1500 g for approximately 10 minutes at approximately 4° C.) to separate the plasma. The plasma can then be frozen at approximately −20° C. or lower for use as blanks in the analysis.

Intestine Samples and Perfusion

Isolated segments (about 30 cm to about 45 cm) of human intestine, immediately below the entry of the bile duct, for example, are preferably removed from hypothermic storage and used for each analysis.

The entire intestine sample is weighed and flushed with cold buffer via the mesenteric artery (or a branch thereof) for about 10 to about 15 minutes, at approximately 4-8° C., at a pH of approximately 7.4 and at a pressure of approximately 60-80 mmHg. This arterial buffer flush generally involves about 0.5 liter of buffer.

Following the arterial buffer flush is the equilibration period, wherein about 0.5 liter of oxygenated room temperature perfusate is passed through the intestine at a rate of approximately 20 ml/min. Approximately 0.5 liter of perfusate effluent is allowed to run to waste and the perfusion then switched to recirculating mode with 0.75 liter of oxygenated perfusate. The perfusion flow rate is preferably increased up to a target of about 90 to about 100 ml/min. over time without exceeding maximum pressure limits. The perfusate is recirculated until the intestinal core temperature is greater than about 35° C. and peristalsis is visible. The first pass and first recirculation combined generally last up to about 60 minutes.

At the end of the equilibration period, the perfusate is drained from the apparatus and replaced with about one liter of fresh oxygenated perfusate at about 37° C. in recirculation mode. This period is the stabilization period, which lasts for about 10 to about 15 minutes. Subsequently, perfusate aliquots are removed provided perfusion and physiological parameters, e.g., oxygen uptake, core temperature more than about 35° C., flow of about 90 ml/min. and pressure between about 60 to about 80 mmHg, are satisfied.

Dosing and Sample Collection

In order to ensure that the intestine is suitable for use in the test, its suitability is preferably checked at this stage. Such a step can avoid wasted time and efforts even where suitability of the organ had been established prior to hypothermic storage. In particular, organs or tissues unduly damaged in storage or perfusion can be eliminated from further testing or baseline properties can be established. Preferred acceptance criteria for normothermic perfusion of human intestine prior to dosing with a test substance are:

| Perfusion & Physiological Parameters | |
|---|---|
| Arterial pressure (mmHg) | 100 |
| Arterial flow (ml/min./gram) | 0.2-1.0 |
| Venous $PO_2$ | >26 |
| Arterial $PO_2$ | >120 |
| pH | 7.3 ± 0.2 |
| Temperature (° C.) | 37.4 ± 2 |
| PCV (% cells) | 20-45% |

The preferably labeled, e.g., radiolabeled, test substance (approximately 10 mg, approximately 100 µCi) and preferably 3-5 labeled internal standards, which are absorbed by passive diffusion at different rates, are administered, preferably as a pulse dose, in the same formulation in a maximum volume of about 15 ml into the lumen of the isolated intestine. This is designated "time zero."

The intestine is then perfused, in recirculating mode, preferably for about 2 hours and aliquots (about 3 to about 5 ml)

of the perfusate are removed, preferably at at least two of the following preferred times: pre-dosing and 5, 10, 15, 30, 45, 60, 90, 105 and 120 minutes post-dosing. Approximately half of each sample is frozen at about −70° C. and the remainder of each sample is centrifuged and the plasma removed and frozen at about −70° C. Alternatively, in five milliliter samples, for example, about 1 milliliter is retained as whole perfusate and the remaining about 4 milliliters centrifuged and the plasma supernatant divided into four approximately equal aliquots for separate analyses.

At termination of the perfusion, the intestinal segments are weighed, lumen contents are collected and weighed, and the lumen is flushed with about 100 milliliters of water and added to the intestinal contents and the combined mass recorded. The mixture is homogenized in a minimum amount of water and frozen for subsequent analysis, if desired, in approximately equal aliquots, such as about 40 milliliter aliquots. In addition, the perfusion apparatus is preferably rinsed with saline, water and/or alcohol. A sample of each rinse can be retained for subsequent analysis (e.g., mass balance).

Embodiments of the perfusion method allow for multiple (single or cassette) dosing into sequential segments of the same intestine. In such embodiments, the entire intestinal segment is perfused, as above, but after equilibration, the intestine (mesentery and lumen) is separated into three segments, preferably of approximately equal length, such that the lumen of each of the three segments is entirely separate, although the perfusate still circulates through each segment and subsequently mixes. One of the segments is then dosed with test substance and standards and aliquots of perfusate removed at timed intervals up to about one hour to about two hours post-dosing. This segment is then removed adjacent to the mesentery by, for example, cauterization, leaving the mesentery intact, but sealed. A liter of fresh perfusate is then flushed through the two remaining segments and the eluant collected in the first pass. Fresh perfusate (about 1 liter to about 1.5 liters) is then added and recirculated at a flow rate of ⅓ less than for 3 segments. The second segment is then dosed and the entire process repeated until all 3 segments have been dosed and aliquots of perfusate collected at timed intervals up to about one hour to about two hours post-dosing for each time zero.

Biopsies

Biopsies are preferably taken pre-dosing and at the termination of the perfusion and flash-frozen in liquid nitrogen at the point of collection prior to the homogenization. The biopsies can be subjected to histopathology and phenotyping for marker enzymes and other proteins.

Controls

Preferred controls include, but are not limited to, aliquots of perfusate and plasma collected pre-dosing. Controls are preferably stored at about −80° C.

Analysis

Absorption of the test substance is determined by analyzing its rate of absorption from the intestinal lumen into the recirculating perfusate with time and comparing the rate with that of the internal standards. The raw data is generally in pmoles/ml, total pmoles and/or percent dose and includes the percent fraction for all absorbed compounds and the mass balance of labeled test substance in the perfusate, plasma, intestinal contents and intestinal wall. If radiolabeled compounds and standards are used, then total radioactivity measurements can be taken, and, if desired, HPLC profiling of the labeled test compound can be performed.

During perfusion, physiological parameters are monitored, such as arterial pressures and flows, organ core temperature, blood pH, active peristalsis and arterial and venous $PO_2$ and $PCO_2$; blood biochemistry parameters, such as electrolyte balance including, but not limited to, concentrations of potassium (mM), sodium (mM), chloride (mM), calcium (mM), albumin (g/dl), ALP (alkaline phosphatase) (U/l), ALT (alanine transaminase) (U/l), amylase (U/l), AST (aspartate transaminase) (U/l), GGT (gamma glutamyl transferase) (U/l), Cal (mg/dl) and BUN (blood urea nitrogen) (mg/dl); biomarkers, such as, glucose (mg/dl) utilization and lactate (mM) production; absorption of internal standards, such as $^3$H-mannitol (target concentration about 100 µCi; target dose about 20 µM), antipyrine (target dose about 20 µM), terbutaline (target dose about 20 µM), dextran (about 10 to about 70 kD) and/or other labeled or unlabeled standards; and presence and characteristics of the test compound and/or metabolites.

Applications of Perfused Intestine Model in Drug Development

Perfusion studies can be used in numerous phases in drug development. For example, absorption studies can be used in assessing single pulse doses and/or repeated doses of a drug candidate, constant infusion, cassette dosing, effects of formulation, regional differences, effects of food, saturation kinetics and drug-drug interactions, for example. Metabolic studies can be used to assess metabolite identification, metabolite quantification, saturation kinetics and regional differences, for example. Distribution studies can be used to assess covalent binding, for example.

Perfused Liver Protocol

Species, strain and gender differences in drug metabolism have been well documented over the last 50 years. In many cases, these differences are attributed to variations in the concentration of intracellular enzymes and cofactors, particularly in the liver. In drug development, the appearance of either new metabolites or vastly different concentrations of particular metabolites from that found in initial studies of a drug candidate can lead to a considerable amount of additional resources and lost time.

Currently, attempts to predict human liver metabolism are performed with data from in vitro preparations, i.e., tissue slices, isolated hepatocytes, S9 fractions or microsomes. Although these studies are important, they sometimes: (a) do not mimic metabolism in the whole liver; (b) identify potential rather than actual metabolism; and (c) give no measure of subsequent partitioning of metabolites between blood and bile, and thus the exposure of extra-hepatic organs and tissues to the biproducts of liver metabolism.

In isolated vascular perfused human liver studies, these shortcomings may be avoided. Instead, test substances and validation standards may be delivered via matched blood-based perfusate at physiological flow rates to a stable, viable hepatic tissue or organ with normal biliary secretory mechanisms. Consequently, this model is ideally suited to determine the nature and extent of drug uptake, drug metabolism and drug clearance in human liver, as well as biliary elimination, mass-balance and measurements of the subsequent partitioning of metabolites between blood and bile. In addition, specific metabolites may be characterized in separate studies.

Exemplary Perfusion Conditions

Approximately five to six liters of perfusate are used per analysis. Fresh perfusate containing human erythrocytes (previously washed and centrifuged) is suspended in buffer containing 6% human serum albumin (at about room temperature, about 15 to about 20% v/v, pH about 7.4). If the test compound is known to bind to α-1-glycoprotein, then 4% human serum albumin is used instead of 6%, plus 2% α-1-glycoprotein. The perfusate is then passed through a Pall 40 micron blood transfusion filter, followed by a "leukocyte-removing" filter, approximately 15 N.I.H. units/ml of heparin are added and the pH adjusted, if necessary, to approximately 7.4. The perfusate is preferably stored at room temperature until added to the perfusion apparatus. An aliquot of the surplus perfusate, such as approximately 50 ml, may be centrifuged (approximately 1500 g for approximately 10 minutes at approximately 4° C.) to separate the plasma and blood cells. This plasma may be frozen at approximately −20° C. or lower for use as blanks in the analysis.

Throughout the perfusion, the flow, pressure and temperature are recorded in the portal vein and the hepatic artery. The $PO_2/PCO_2$ is measured at approximately 15 minute intervals in the inlets via the hepatic artery and portal vein and in the outlet via the vena cava. Each liver is allowed an equilibration period of about 45 to about 60 minutes and bile is collected in pre-weighed containers. Only satisfactory preparations, in terms of perfusate flow and pressure and bile flow are dosed with test substances.

Supplementary bile salts are added initially to the perfusate and then throughout the perfusion period. Bile salts include, but are not limited to, about 1 gram of sodium glycocholate hydrate (Sigma G7132), about 0.5 gram sodium glycodeoxychoate (Sigma G9910) and sodium glychochenodeoxycholate (Sigma G0795) dissolved in 25% hydroxypropyl beta cyclodextrin (HPβCD), wherein the total mass of bile salt in the HPβCD solution is 20 g. About 1 gram of bile salt HPβCD solution per liter of perfusate is preferred initially, followed by about 1 gram of solution into the perfusate at 1, 2, 3, 4 and 5 hours. Thus, the perfusate will be comprised of washed matched human erythrocytes suspended in human plasma supplemented with bile salts.

Perfused Liver Samples

An isolated human liver is removed from hypothermic storage and, if possible, the hepatic artery, portal vein and vena cava are cannulated. The liver is then flushed at about room temperature with about one liter to about two liters of cold buffer, such as Krebs-Ringer bicarbonate buffer (pH approximately 7.4), under gravity, for about 10 to about 15 minutes, to remove the transport/storage medium.

About 1.5 liters of fresh perfusate containing human erythrocytes (previously washed) suspended in buffer containing 4% or 6% human serum albumin, as described above, at about room temperature, about 15 to about 20% v/v, pH about 7.4, are then pumped at approximately 20 ml/min. into the hepatic artery and portal vein and allowed to recirculate for about 45 to about 60 minutes in an equilibration phase.

After approximately 1 liter has run to waste, about two liters of fresh perfusate are recirculated within the perfusion apparatus. The temperature of the perfusate is raised to about 37° C. and perfusion flow rates are increased to target flow rates, e.g., about 200 to about 300 ml/min. through the hepatic artery and about 400 to about 800 ml/min., preferably about 600 ml/min., through the portal vein for about 10 to about 15 minutes in a stabilization phase.

Dosing and Sample Collection

The solubility and stability of the test compound are preferably confirmed prior to the perfusion study as described above. Once the perfusion preparations are stable with respect to perfusate flow and pressure, the test substance is added to the recirculating perfusate. Preferred acceptance criteria for normothermic perfusion of human liver prior to dosing with a test substance are:

| Perfusion & Physiological Parameters | |
|---|---|
| Arterial pressure (mmHg) | 40-60 |
| Arterial flow (ml/min.) | 200-300 |
| Portal pressure (mmHg) | 15-22 |

-continued

| Perfusion & Physiological Parameters | |
|---|---|
| Portal flow (ml/min.) | 600-800 |
| Venous $PO_2$ | >26 |
| Arterial $PO_2$ | >120 |
| PH | 7.3 ± 0.2 |
| Temperature (° C.) | 36.5 ± 2 |
| PCV (% cells) | 15-20 |

The dosing vehicle is preferably aqueous, or in the case of compounds with poor aqueous solubility, is DMSO at a final concentration of about 0.1% v/v in perfusate. The preferred dosing regime comprises adding about 50 mg of, preferably, labeled, such as radiolabeled, test compound or a mixture of non-labeled and labeled, such as radiolabeled, test compounds, in DMSO as an infusion into the perfusate over a period of time (median Tmax=about 1 hour). If radiolabels are used, the target radioactive dose is preferably about 100 µCi per liver.

Each dosing solution is preferably put into a pre-weighed syringe with an attached cannula and the syringe is reweighed. The contents of the syringe are expelled as a pulse dose into the perfusate. The test compound is added at designated "time zero" and the liver perfused for about 240 minutes. A standard, such as tetra-BSP (about 20 µM), is added at the end of the about 240 minutes and the liver is perfused for about 120 minutes more. The liver is perfused for about six hours in total post-dosing. Perfusate samples (about 10 ml per sample) are collected, for example, at at least two of the following times during perfusion: pre-dose and 5, 10, 15, 30, 45, 75, 105, 135, 165, 195, 225 and 239 minutes post-dose.

In addition, bile is continuously collected throughout the perfusion, for example, at at least two of the following times: pre-dose and 30, 60, 90, 120, 150, 180, 210 and 240 minutes post-dose.

The liver is dosed with at least one positive control at about four hours after "time zero" and the perfusate sampled, for example, at at least two of the following times: 245, 150, 255, 270, 285, 300, 330 and 360 minutes past time zero.

From each about 10 ml sample, about 1 milliliter is retained as whole perfusate and the remaining about 9 milliliters centrifuged and the plasma supernatant divided into four approximately equal aliquots. The supernatants and bile samples can be stored at about −80° C. until analyzed for dosed test and control compound and any metabolites. Following sampling of each about 10 ml aliquot, about 10 ml of control perfusate (perfusate without the test substance) is added to the perfusion system to maintain a constant volume.

At perfusion termination, all the remaining perfusate and apparatus washings are collected for mass-balance analysis and/or metabolite profiling, if desired (in perfusate/plasma). The gall bladder, if not dissected from the liver prior to the perfusion, can be homogenized and assayed for total radioactivity, assuming the test compound and/or one of more control is radiolabeled.

After the tissue is collected, the perfusion apparatus is preferably rinsed with saline and, at the end of the perfusion, with water and alcohol. A sample of each rinse is preferably retained for analysis. In addition, the dosing syringe and cannula are reweighed after dosing and washed with water and methanol. The syringe/cannula washing is assayed for radioactivity, if applicable, or other label, if applicable. The test compound dose administered is calculated by subtracting the syringe washings from the total amount of radioactivity, for example, taken-up into the syringe/cannula.

Biopsies

Biopsies are preferably taken pre-dose and at 360 minutes post-dose and flash-frozen in liquid nitrogen at the point of collection. The remainder of the liver is homogenized at the end of the perfusion. The biopsies can be subjected to histopathology and phenotyping for marker enzymes and other proteins.

Controls

Preferred control samples include, but are not limited to, aliquots of bile, perfusate and plasma collected pre-dose, and, if possible, liver homogenates collected from a separate organ. All samples are preferably stored at about −80° C.

Analysis

If radiolabeled compounds and standards are used, then total radioactivity measurements can be taken, and, if desired, extraction and HPLC profiling of the labeled test compound, standards and/or metabolites can be performed. In addition, possible structural identification may be performed on metabolites and extraction and analysis of the standard, such as tetra-BSP and its glutathione conjugates in plasma and bile, can be conducted.

During perfusion, physiological parameters may be monitored, such as arterial pressure and flow, organ core temperature, blood pH and arterial and venous $PO_2$ and $PCO_2$; blood biochemistry parameters such as electrolytes including, but not limited to, potassium (mM), sodium (mM), chloride (mM), calcium (mM), albumin (g/dl), ALP (U/l), ALT (U/l), amylase (U/l), AST (U/l), GGT (U/l), Cal (mg/dl), bilirubin (U/l) and BUN (mg/dl); biomarkers such as glucose (mg/dl) utilization and lactate (mM) production; absorption of standards such as $^3$H-mannitol, antipyrine, propanalol, atenolol, bromosulphophthalein (tetra-BSP), 1-naphthol, 7-ethoxycoumarin, terbutaline and/or other labeled or unlabeled standards; and presence and characteristics of the test compound and/or metabolite(s) in bile, perfusate and liver.

Applications of Perfused Liver Model in Drug Development

Perfusion studies can be used in numerous phases in drug development. For example, first pass clearance and/or plasma clearance studies can be used to assess a test compound's half-life, single pulse dosing, repeated pulse dosing, plasma steady state and cassette dosing. Biliary excretion can be used to quantify the parent drug (substance being tested) or to assess saturation kinetics, for example. Metabolic studies can be used to assess metabolite identification, metabolite quantification, partitioning of metabolites between plasma and bile and saturation kinetics, for example. Distribution studies can be used to assess tissue clearance, drug-drug interaction and covalent binding, for example. Hepatic uptake, distribution, tissue accumulation (drug accumulation in tissue) metabolism and/or excretion studies can be used to study hepatic diseases.

Perfused Kidney Protocol

The ability to determine qualitatively and quantitatively the fates and effects of drug candidates in human kidneys, prior to clinical trials, is important in drug development. Processes of particular relevance to drug development include, but are not limited to: (a) renal clearance, plasma clearance, and glomerular filtration rate—urine is the principle route of drug elimination and the kidneys are a major site for drug-drug interactions; (b) metabolism—the kidneys have significant Phase I and Phase II drug metabolizing activities such as determining percent tubular reabsorption or active secretion; and (c) distribution—the partitioning of metabolites formed in the kidneys between blood and urine can dictate the subsequent exposure of other organs to pharmacologically active or toxic metabolites.

As with all human organs, the validation process for isolated perfused human kidneys (IPHK) is designed for both hypothermic preservation perfusion after excision of the kidney from the donor and normothermic physiological perfusion for drug research and development.

Preferably, prior to testing using IPHK, as much as possible is known about the history of each kidney in the test and, more importantly, its current condition compared with a database of hundreds of kidneys that were successfully transplanted and those that were not. This is the mechanism by which kidneys are accepted for drug research and the rationale for each decision is recorded. However, using the present disclosure, the kidneys need not be in the same condition as they would need to be in for transplantation. Thus, e.g., organs from older donors than would be accepted for transplantation (e.g., older than 56 years) and from non-beating-heart donors, as well as diseased and injured organs, may be used.

Perfusion Conditions

Donated kidneys are transferred to hypothermic storage as soon as possible after collection and perfused with a buffer, such as KPS-1® buffer (Organ Recovery Systems, Inc., Des Plaines, Ill.), at about 6 to about 8° C. for a minimum of about 4 hours.

The kidney(s) is then flushed with about 1 liter of fresh perfusate and the temperature of the perfusate effluent raised to about 37° C. When the kidney(s) is stable with respect to perfusion pressure and flow and urine formation, the first perfusate is replaced with about 1.5 liters of fresh perfusate.

In embodiments, the perfusate used for kidney perfusions is derived from a liver perfusion experiment in which a test compound has been perfused through a human liver. In this way the renal handling and/or further metabolism of hepatic metabolites of the test substance and standards can be resolved.

Dosing and Sample Collection

Preferred acceptance criteria for normothermic perfusion of human kidneys prior to dosing with a test substance are:

| Perfusion & Physiological Parameters | |
| --- | --- |
| Perfusion pressure (mmHg) | 40-80 |
| Perfusate flow rate (ml/min.) | 250-450 |
| PH | 7.4 ± 0.3 |
| Temperature (° C.) | 36.5 ± 2 |
| Glomerular filtration rate (GFR) (ml/min.) | 20-80 |
| Venous $PO_2/PCO_2$ | 20-50/5-30 |
| Arterial $PO_2/PCO_2$ | 120-140/5-30 |
| PCV (% cells) | 16-22 |

The test substance and internal standards are dosed directly into the perfusate and aliquots of perfusate (about 3 ml to about 5 ml) are taken about every 15 minutes and urine collected batchwise about every 15 minutes for about 2 hours. Each perfusate sample is subdivided into four approximately equal aliquots. Two aliquots are retained for analysis and the other two centrifuged and the plasma removed and stored frozen at about −70° C. for additional analysis if required. Urine samples are collected into tarred tubes, weighed and frozen at about −70° C. for subsequent analysis of, for example, test compounds, standards and metabolites.

After the test compound has been administered to an IPHK for sufficient time, for example, about 60 minutes, exogenous positive controls can be added to the circulating perfusate to validate those critical processes not covered by endogenous compounds, i.e., the internal standards. These additional, preferably labeled, controls include, but are not limited to, p-amino hippuric acid (for assessing tubular secretion) and a glutathione conjugate (for assessing the integrity of the mercapturic acid pathway).

Perfusate and urine samples are collected about every 30 minutes for a further about 2 hours after dosing the positive controls and are retained for analysis, which includes, but is not limited to, measuring physiological parameters; measuring blood chemistry parameters, such as potassium (mM), sodium (mM), chloride (mM), calcium (mM), glucose (mg/dl), lactate (mM), albumin (g/dl), ALP (U/l), ALT (U/l), amylase (U/l), VAG (U/l), AST (U/l), γ-GST (glutathione S-transferase) (U/l), creatinine (mg/dl) and urinary excretions (U/l); measuring test compounds, standards and/or metabolites in urine, perfusate and kidney; and measuring parameters of urine biochemistry, such as N-acetylglucosaminidase, glutathione S-transferase and proteins and peptides.

Applications of Perfused Kidney Model in Drug Development

Perfusion studies can be used in numerous phases in drug development. For example, plasma clearance studies can be used to assess single pulse dosing, repeated pulse dosing, single compound dosing, plasma steady state, cassette dosing and saturation kinetics. Renal excretion can be used to assess GFR, test compound percent reabsorbed, test compound percent secreted, saturation kinetics, and drug-drug interactions for example. Metabolic studies can be used to assess metabolite identification, metabolite quantification, partitioning of metabolites between plasma and urine and saturation kinetics, for example. Distribution studies can be used to assess regional distribution and covalent binding, for example.

Perfused Human Lung Protocol

The isolated perfused human lung preparation (IPHLung) is a versatile system for studying lung specific drug-related activities including, but not limited to, assessing inhaled drug performance by quantitating ventilatory function, drug preparation stability, drug absorption via the airways, drug uptake from the blood, drug metabolism, clearance and retention, extent of edema, pharmacological effects, drug efficacy, drug toxicity and drug-drug interactions, as well as assessing physiologic function and pharmacologic responsiveness of the lungs by inducing bronchoconstriction/dilation with histamine/salbutamol, or other internal standard, using nebulized delivery. Reliable quantification of one or more of these activities can provide the basis for key decision making in drug candidate selection and/or problem solving, if necessary, after test compounds are released into the market.

Moreover, perfusion studies overcome numerous problems of in vitro lung studies, including, but not limited to, allowing for the over 40 cell types in the lung, many of which cannot be isolated and many of which change their phenotype when cultured.

Perfusion Conditions

Preferably, a pair of respiring lungs is flushed free of donor blood with about 2 liters of buffer, such as Krebs-Ringer buffer, at about 6 to about 8° C. at about 12 to about 18 ml/min. The lungs are then perfused via the pulmonary artery with fresh perfusate with a pressure of less than about 18 mmHg and the flow continuously recorded. The effluent from the pulmonary veins can be recirculated (except under first-pass conditions). About two liters of perfusate are used for the perfusion study.

Preferred biomarkers are enzymatic, including, but not limited to, angiotensin converting enzyme. Preferred internal standards include, but are not limited to, about 1 mg/ml salbutamol or other bronchodilator (dose of about 150 µg), about 1 mg/ml ipatropium (dose of about 150 µg) and polyamines.

Dosing and Sample Collection

Preferred acceptance criteria for normothermic perfusion of human lungs prior to dosing with a test substance are:

| Perfusion & Physiological Parameters | |
|---|---|
| Perfusion pressure (mmHg) | ≤18 |
| Perfusate flow rate (ml/min.) | 1000-3000 |
| pH | 7.4 ± 0.3 |
| Temperature (° C.) | 37.0 ± 1 |
| Airflow (l/min.) | at least 66 |
| Tidal volume (ml) | 500-1000 |
| Lung Function Tests | @ about 10-20 second intervals |

Pre-dose and at other sample times, perfusate samples are taken and blood chemistry is assessed in terms of, for example, pH, $pCO_2$, lactate and inorganic ions. In addition, samples are taken at the same times to assess the release of angiotensin converting enzyme and other enzymes After dosing of the test compound or cassette of compounds (via the airway using a nebulizer or into the perfusate) at a concentration of about 0.3 to about 1.0 mg/ml (dosage of about 45 to about 150 µg) (referred to as "time zero"), aliquots (preferably about 3 to about 5 ml) of perfusate are removed pre-dose and at at least two of the following times: 5, 10, 15, 30, 45, 60, 90 and 120 minutes post-dose for absorption studies, for example. About 1 ml of each aliquot is retained for blood chemistry/biochemistry and hematocrit measurements. A portion of the remaining aliquot is set aside (about 1 ml whole perfusate) and the remainder is centrifuged and the resulting cell-free supernatant further divided into aliquots, which are flash frozen in liquid nitrogen at the point of collection.

After about 120 minutes post-dose, the perfusate is replaced with fresh perfusate, which is circulated for about 30 minutes. Perfusate samples (about 3 to about 5 ml aliquots) are taken at, for example, 5, 10, 15 and 30 minutes from the beginning of the fresh perfusate circulation. About 1 ml of each aliquot is retained for blood chemistry/biochemistry and hematocrit measurements. A portion of the remaining aliquot is set aside (about 1 ml whole perfusate) and the remainder is centrifuged and the resulting cell-free supernatant further divided into aliquots, which are flash frozen in liquid nitrogen at the point of collection.

At the end of the 30 minutes, metabolic markers are added to the perfusate and the perfusate is again sampled at, for example, 5, 15, 30 and 60 minutes (to the end of the perfusion and/or at other time points, if feasible) after metabolic marker addition in about 3 to about 5 ml aliquots, which are subsequently frozen for later analysis of test compounds and metabolites. About 1 ml samples of plasma are also taken at, for example, 5, 15, 30 and 60 minutes (and other time points as feasible) after metabolic marker addition for polyamine uptake determination. Markers include, but are not limited to, probes added to the perfusate, ethoxycoumarin (CYP1A) at a dose of about 20 µM, and 1-naphthol (glucuronidation and sulfation) at a dose of about 10 µM.

At about three hours and 30 minutes from time zero, histamine, or other bronchoconstrictor or vasodilator, is added to the perfusate at a concentration of about $10^{-5}$ M to about $10^{-6}$ M for a pharmacology evaluation. About ten minutes later, bronchoconstriction is assessed. If evidence of bronchoconstriction is not found, then histamine is again added, but at an increased concentration of about $10^{-6}$ M to about $10^{-5}$ M, respectively. Increased concentrations of histamine are added to the perfusate every ten minutes until evidence of bronchoconstriction is apparent at which time inhalation of a control, such as salbutamol, is initiated at a dosage of 2×150 µg from 1 mg/ml stock solution. Preferably dosing is performed using a ProDose device with a 150 µl disk. The presence of bronchodilation is determined over about 15 minutes. Papaverine or other vasodilator may then be added to the perfusate at a concentration of about $10^{-7}$ M and the extent of bronchodilation determined.

Biopsies

Histology studies can be performed on each lung using a container, such as a 500 ml plastic screw-top container, filled with neutral buffered formalin, for example. The lung lobes are removed with the entire length of the bronchus, avoiding damage to the parenchymal tissue. A ligature is loosely placed around the bronchus. The bronchus can be held with forceps and a syringe used to slowly insufflate the entire lung lobe with formalin. Insufflation is discontinued after the lobe is expanded 75%. The bronchus is ligated and the lobes are placed in the formalin. The date and time of this initial fixation are noted.

Applications of Perfused Lung Model in Drug Development

Perfusion studies can be used in numerous phases in drug development. For example, absorption studies (via the airways) can be used to assess formulations of the test compound, such as liquid, dry powder or nebulizer, and dosing regimens, such as single dosing, repeat dosing or cassette dosing. Plasma clearance studies can be used to assess single pulse dosing, repeated pulse dosing, single compound dosing, cassette dosing and constant infusion dosing, for example. Metabolic studies can be used to assess metabolite identification, metabolite quantification, volatile metabolites and saturation kinetics, for example. Distribution studies can be used to assess accumulation of the test compound in tissues, residence times and transit times, for example.

In the practice of the methods of this invention, devices and apparatus for perfusing organs for transplant can be used, as disclosed in co-owned U.S. Pat. No. 6,673,594 and U.S. published patent application No. 2004/0224298, each of which is expressly incorporated by reference in its entirety herein. However, one of ordinary skill in the art will recognize that there are differences in the way tissues and organs may be used according to the inventive methods and the way tissues and organs are maintained by perfusion for organ transplantation.

All patents, patent applications, scientific article and other sources and references cited herein are explicitly incorporated by reference herein for the full extent of their teachings as if set forth in their entirety explicitly in this application.

It should be understood that the foregoing disclosure emphasizes certain specific embodiments of the invention and that modifications or alternatives equivalent thereto are within the spirit and scope of the invention.

What is claimed is:

1. An ex vivo method of validating results of substance testing using at least one human organ or tissue unsuitable for transplantation, wherein said human organ or tissue is a metabolically active human organ or tissue that has been permanently removed from its origin, the method comprising:

(a) assessing said human organ or tissue for suitability for testing prior to administration of a test substance by perfusing said organ or tissue under physiological and normothermic conditions with a perfusate that comprises about 15 to about 20% (v/v) matched human erythrocytes, about 2 to about 6% human serum albumin, N-acetylcysteine and adenosine monophosphate (AMP), but does not comprise the test substance, wherein assessing said human organ or tissue for suitability includes determining that said human organ or tissue is unsuitable for transplantation, and either assaying the perfusate after it leaves said organ or tissue, or monitoring a parameter of said organ or tissue;

(b) preparing a perfusate comprising said test substance, about 15 to about 20% (v/v) matched human erythrocytes, about 2 to about 6% human serum albumin, N-acetylcysteine and adenosine monophosphate (AMP), and perfusing said organ or tissue under said conditions with the perfusate containing the test substance;

(c) assessing a parameter relating to said test substance;

(d) assessing said organ or tissue for suitability for testing of said parameter relating to said test substance during and/or after administration of said test substance by quantifying a functional state of said organ or tissue relative to said parameter being assessed, wherein said organ or tissue acts as its own control, verifying that the organ or tissue is still having its effect, or being affected by, substances in connection with said parameter being assessed for the test substance, and verifying that said parameter being assessed is not inappropriately affected by an extraneous change in the organ or tissue during the course of assessment of the parameter relating to said test substance; and wherein quantifying the functional state of said organ or tissue relative to said parameter being assessed in step (d) comprises perfusing said organ or tissue under same conditions with the same perfusate comprising about 15 to about 20% (v/v) matched human erythrocytes, about 2 to about 6% human serum albumin, N-acetylcysteine and adenosine monophosphate (AMP), and additionally containing at least one control substance having a known qualitative or quantitative effect with respect to said parameter, and assessing the same parameter with respect to at least one said control substance.

2. The method of claim 1, wherein said control substance has a competitive relationship with said test substance relative to said parameter, and is perfused through the organ or tissue after the test substance has been perfused through the organ or tissue.

3. The method of claim 1, wherein said control substance has a competitive relationship with said test substance relative to said parameter, and is perfused through the organ or tissue simultaneously with the test substance.

4. The method of claim 1, wherein said control substance has a non-competitive relationship with said test substance relative to said parameter, and is perfused through the organ or tissue simultaneously with the test substance.

5. The method of claim 1, wherein step quantifying the functional state of said organ or tissue relative to said parameter being assessed in step (d) comprises perfusing said organ or tissue with the same perfusate additionally containing at least two control substances having a known qualitative or quantitative effect with respect to said parameter, and assessing the same parameter with respect to at least two said control substances.

6. The method of claim 5, wherein a value of said parameter for a first said control substance has previously been established to be significantly different from a value of said parameter for a second said control substance.

7. The method of claim 6, wherein the value of said parameter for the first said control substance has previously been established to be zero or near zero, and the value of said parameter for the second said control substance has previously been established to be substantially different from zero.

8. The method of claim 6, wherein said parameter is plasma clearance of the substance by liver, and the at least two control substances are propanolol and atenolol.

9. The method of claim 6, wherein said parameter is uptake of the substance by heart, and the at least one control substance is selected from the group consisting of dopa and dopamine.

10. The method of claim 1, further comprising determining a ratio between a first value of said parameter for said test substance and a second value of said parameter for said control substance.

11. The method of claim 10, comprising performing said method on a plurality of the same type of organ, establishing a normative range of said ratios, and discounting results of tests in which the ratio is outside of said normative range of ratios.

12. The method of claim 1, wherein said parameter is passive absorption of the substance by organs of the type tested.

13. The method of claim 12, wherein the organs of the type tested are intestines, and the at least one control substance is at least one member selected from the group consisting of antipyrine, terbutaline, mannitol and labeled dextrans.

14. The method of claim 1, wherein said parameter is active absorption of the substance by organs of the type tested, and said at least one control substance is perfused through the organ or tissue after the test substance has been perfused through the organ or tissue.

15. The method of claim 14, wherein the organs of the type tested are intestines, and the at least one control substance is at least one member selected from the group consisting of cephalexin and arginine.

16. The method of claim 14, wherein the organs of the type tested are lungs, and the at least one control substance is selected from the group consisting of salbutamol and ipratropium.

17. The method of claim 1, wherein said parameter is phase I metabolism of the substance by organs of the type tested.

18. The method of claim 17, wherein the organs of the type tested are intestines or kidneys, and the at least one control substance is at least one member selected from the group consisting of phenacetin, tolbutamide, s-methenyltoin, dextromethorphan, chloroxazone and methadone.

19. The method of claim 17, wherein the organs of the type tested are livers, and the at least one control substance is at least one member selected from the group consisting of phenacetin, tolbutamide, s-methenyltoin, dextromethorphan, chloroxazone, methadone, carbamazepine and 7-nitrazepam.

20. The method of claim 17, wherein the organs of the type tested are lungs, and the at least one control substance is at least one member selected from the group consisting of phenacetin, tolbutamide, s-methenyltoin, dextromethorphan, chloroxazone, methadone and carbamazepine.

21. The method of claim 17, comprising selecting said control substance as a function of a type of enzymatic metabolism suspected to occur with said test substance.

22. The method of claim 1, wherein said parameter is phase II metabolism of the substance by organs of the type tested.

23. The method of claim 22, wherein the organs of the type tested are selected from the group consisting of intestines, livers, lungs and kidneys, and the at least one control substance is at least one member selected from the group consisting of harmol and naphthol.

24. The method of claim 1, wherein said parameter is biliary excretion of the substance by liver, the at least one control substance is at least one member selected from the group consisting of tetrabomosulphophthalein, dibromosulphophthalein, indocyanine green and bile salts, and said at least one control substance is perfused through the organ or tissue after the test substance has been perfused through the organ or tissue.

25. The method of claim 1, wherein said parameter is receptor mediated endocytosis of the substance by liver, and the at least one control substance is at least one member selected from the group consisting of asialoglycoproteins.

26. The method of claim 1, wherein said parameter is active uptake of the substance by lung, and the at least one control substance is at least one member selected from the group consisting of putrescine, spermine and spermidine, and said at least one control substance is perfused through the organ or tissue after the test substance has been perfused through the organ or tissue.

27. The method of claim 1, wherein said parameter is glomerular filtration of the substance by kidney, and the at least one control substance is at least one member selected from the group consisting of inulin and creatinine.

28. The method of claim 27, wherein said control substance is radioactively labeled inulin.

29. The method of claim 1, wherein said parameter is active secretion of the substance by kidney, and the at least one control substance is p-aminohippuric acid, and said at least one control substance is perfused through the organ or tissue after the test substance has been perfused through the organ or tissue.

30. The method of claim 1, wherein said parameter is active reabsorption of the substance by kidney, and the at least one control substance is selected from the group consisting of tetra-ethylammonium acetate, sodium and glucose, and said at least one control substance is perfused through the organ or tissue after the test substance has been perfused through the organ or tissue.

31. The method of claim 1, wherein said parameter is Phase II metabolism of the substance by kidney, and the at least one control substance is at least one member selected from the group consisting of mercaptans and glutathione conjugates.

32. The method of claim 1, wherein said control substance is an endogenous substance.

33. The method of claim 1, wherein said control substance is an exogenous substance.

34. The method of claim 1, wherein said organ or tissue has been subjected to hypothermic storage before step (a).

35. The method of claim 1, wherein said organ or tissue has been subjected to disease or injury before step (a).

36. The method of claim 35, wherein said disease or injury occurred before harvest of said organ or tissue.

37. The method of claim 35, wherein said disease or injury occurred after harvest of said organ or tissue.

38. The method of claim 1, wherein said organ or tissue has been subjected to injury before step (a), and said injury resulted from prolonged warm ischemia.

39. The method of claim 1, wherein said organ or tissue has been subjected to injury before step (a), and said injury resulted from hypothermic storage.

40. The method of claim 1, wherein said at least one organ or tissue is a combination of organs.

41. The method of claim 1, wherein said at least one organ or tissue is an organ or tissue harvested from a deceased human.

42. The method of claim 1, wherein said parameter is assessed in at least one member selected from the group consisting of a perfusate sample, a biopsy from said at least one organ or tissue, and an effluent of said at least one organ or tissue.

* * * * *